(12) United States Patent
Mertens et al.

(10) Patent No.: US 8,268,277 B2
(45) Date of Patent: Sep. 18, 2012

(54) SYNTHESIS OF CHABAZITE-CONTAINING MOLECULAR SIEVES AND THEIR USE IN THE CONVERSION OF OXYGENATES TO OLEFINS

(75) Inventors: Machteld M. Mertens, Boortmeerbeek (BE); Stephen N. Vaughn, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 522 days.

(21) Appl. No.: 12/477,808

(22) Filed: Jun. 3, 2009

(65) Prior Publication Data

US 2010/0022722 A1 Jan. 28, 2010

Related U.S. Application Data

(60) Provisional application No. 61/083,749, filed on Jul. 25, 2008, provisional application No. 61/083,775, filed on Jul. 25, 2008, provisional application No. 61/083,760, filed on Jul. 25, 2008, provisional application No. 61/083,765, filed on Jul. 25, 2008.

(51) Int. Cl.
*C01B 37/08* (2006.01)

(52) U.S. Cl. ............. 423/305; 423/328.2; 423/329.1; 423/702; 423/706

(58) Field of Classification Search ............ 423/702, 423/704, 705, 706, 708, 709, 710, 305, 328.2, 423/329.1
See application file for complete search history.

(56) References Cited

U.S. PATENT DOCUMENTS

| | | | |
|---|---|---|---|
| 3,030,181 A | 4/1962 | Milton | |
| 4,440,871 A | 4/1984 | Lok et al. | |
| 5,191,141 A | 3/1993 | Barger et al. | |
| 5,879,655 A | 3/1999 | Miller et al. | |
| 6,042,808 A * | 3/2000 | Verduijn et al. | 423/709 |
| 6,162,415 A | 12/2000 | Liu et al. | |
| 6,534,692 B1 | 3/2003 | Barger et al. | |
| 6,620,983 B1 | 9/2003 | Cao et al. | |
| 6,793,901 B2 | 9/2004 | Cao et al. | |
| 6,835,363 B1 | 12/2004 | Strohmaier | |
| 6,903,240 B2 * | 6/2005 | Mertens et al. | 585/639 |
| 6,953,767 B2 | 10/2005 | Janssen et al. | |
| 7,067,108 B2 * | 6/2006 | Mertens et al. | 423/709 |
| 7,160,831 B2 * | 1/2007 | Vaughn et al. | 502/64 |
| 7,247,287 B2 | 7/2007 | Cao et al. | |
| 7,544,851 B2 | 6/2009 | Mertens et al. | |
| 7,670,589 B2 * | 3/2010 | Cao et al. | 423/706 |
| 7,754,187 B2 * | 7/2010 | Cao et al. | 423/706 |
| 7,842,640 B2 * | 11/2010 | Mertens et al. | 502/208 |
| 7,901,649 B2 * | 3/2011 | Mertens et al. | 423/306 |
| 7,901,664 B2 * | 3/2011 | Cao et al. | 423/705 |
| 8,048,402 B2 | 11/2011 | Cao et al. | |
| 2004/0215044 A1 * | 10/2004 | Mertens et al. | 585/639 |
| 2004/0253163 A1 | 12/2004 | Cao et al. | |
| 2006/0100472 A1 | 5/2006 | Mertens et al. | |
| 2007/0249492 A1 * | 10/2007 | Mertens et al. | 502/214 |
| 2008/0216650 A1 * | 9/2008 | Falconer et al. | 95/51 |

FOREIGN PATENT DOCUMENTS

| | | |
|---|---|---|
| EP | 1 511 689 | 3/2005 |
| GB | 868846 | 5/1961 |
| WO | 02/070407 | 9/2002 |
| WO | 03/106342 | 12/2003 |
| WO | WO 2004/096709 | 11/2004 |

OTHER PUBLICATIONS

Breck, "Zeolite Molecular Sieves," John Wiley & Sons, 1973.
Breck, "*Chemical Studies in the Biosynthesis of Purine Nucleotides*," J. Chem. Soc., p. 2822 (1956).
Wilson, et al., "*The Characteristics of SAPO-34 which Influence the Conversion of Methanol to Light Olefins*," Microporous and Mesoporous Materials, vol. 29, (1999), pp. 117-126.
Lee et al., "*Methanol Conversion on SAPO-34 Catalysts Prepared by Mixed Template Method*," Applied Catalyis, vol. 329 (2007), pp. 130-136.

* cited by examiner

*Primary Examiner* — David M Brunsman
(74) *Attorney, Agent, or Firm* — David M. Weisberg; Kevin M. Faulkner

(57) ABSTRACT

In a method of synthesizing a silicoaluminophosphate molecular sieve having 90+% CHA framework-type character, a reaction mixture is prepared comprising sources of water, silicon, aluminum, and phosphorus, as well as an organic template. In one aspect, the reaction mixture is heated at more than 10° C./hour to a crystallization temperature and is retained at the crystallization temperature or within the crystallization temperature range for a crystallization time from 16 hours to 350 hours to produce the silicoaluminophosphate molecular sieve. In another aspect, the reaction mixture is heated at less than 10° C./hour to a crystallization temperature from about 150° C. to about 225° C. and is then retained there for less than 10 hours to produce the silicoaluminophosphate molecular sieve. The molecular sieve can then be recovered from the reaction mixture and, preferably, used in a hydrocarbon conversion process, such as oxygenates to olefins.

10 Claims, 7 Drawing Sheets

Comparative Example with Si/Al$_2$ ratio in mixture of 0.11

2 μm

Comparative Example with Si/Al$_2$ ratio in mixture of 0.12

2 μm

Comparative Example with Si/Al$_2$ ratio in mixture of 0.13

2 μm

Comparative Example with Si/Al$_2$ ratio in mixture of 0.14

2 μm

Example with Si/Al$_2$ ratio in mixture of 0.11

2 μm

Example with Si/Al$_2$ ratio in mixture of 0.12

2 μm

Example with Si/Al₂ ratio in mixture of 0.13

Example with Si/Al₂ ratio in mixture of 0.14

Example with Si/Al$_2$ ratio in mixture of 0.05 recovered after zero hours crystallization at 170°C [sample 5A]

2 μm

Example with Si/Al$_2$ ratio in mixture of 0.05 recovered after 10 hours crystallization at 170°C [sample 5B]

2 μm

Average prime olefine selectivity in MTO reaction at 500°C for Comparative Examples E-H and Examples 6-9

Comparative Example with Si/Al$_2$ ratio in mixture of 0.05

Example with Si/Al$_2$ ratio in mixture of 0.04

Average prime olefin selectivity in MTO reaction at 525°C
for Comparative Examples K-M and Examples 10-13

SYNTHESIS OF CHABAZITE-CONTAINING MOLECULAR SIEVES AND THEIR USE IN THE CONVERSION OF OXYGENATES TO OLEFINS

CROSS-REFERENCE TO RELATED APPLICATIONS

The present application is related to, and claims priority to, U.S. Ser. No. 61/083,749, U.S. Ser. No. 61/083,775, U.S. Ser. No. 61/083,760, and U.S. Ser. No. 61/083,765, each filed on Jul. 25, 2008 and entitled, "Synthesis of Chabazite-Containing Molecular Sieves and Their Use in the Conversion of Oxygenates to Olefins," the entire disclosures of each of which are hereby incorporated by reference herein.

FIELD OF THE INVENTION

This invention relates to the synthesis of chabazite-type containing molecular sieves and their use in the conversion of oxygenates, particularly methanol, to olefins, particularly ethylene and/or propylene.

BACKGROUND OF THE INVENTION

The conversion of oxygenates to olefins (OTO) is currently the subject of intense research because it has the potential for replacing the long-standing steam cracking technology that is today the industry-standard for producing world scale quantities of ethylene and propylene. The very large volumes involved suggest that substantial economic incentives exist for alternate technologies that can deliver high throughputs of light olefins in a cost efficient manner. Whereas steam cracking relies on non-selective thermal reactions of naphtha range hydrocarbons at very high temperatures, OTO exploits catalytic and micro-architectural properties of acidic molecular sieves under milder temperature conditions to produce high yields of ethylene and propylene from methanol.

Current understanding of the OTO reactions suggests a complex sequence in which three major steps can be identified: (1) an induction period leading to the formation of an active carbon pool (alkyl-aromatics), (2) alkylation-dealkylation reactions of these active intermediates leading to products, and (3) a gradual build-up of condensed ring aromatics. OTO is therefore an inherently transient chemical transformation in which the catalyst is in a continuous state of change. The ability of the catalyst to maintain high olefin yields for prolonged periods of time relies on a delicate balance between the relative rates at which the above processes take place. The formation of coke-like molecules is of singular importance because their accumulation interferes with the desired reaction sequence in a number of ways. In particular, coke renders the carbon pool inactive, lowers the rates of diffusion of reactants and products, increases the potential for undesired secondary reactions and limits catalyst life.

Over the last two decades, many catalytic materials have been identified as being useful for carrying out the OTO reactions. Crystalline molecular sieves are the preferred catalysts today because they simultaneously address the acidity and morphological requirements for the reactions. Particularly preferred materials are eight-membered ring aluminosilicates, such as those having the chabazite (CHA) framework type, as well as aluminophosphates (AlPOs) and silicoaluminophosphates (SAPOs) of the CHA framework type, such as SAPO-34.

Chabazite is a naturally occurring zeolite with the approximate formula $Ca_6Al_{12}Si_{24}O_{72}$. Three synthetic forms of chabazite are described in "Zeolite Molecular Sieves", by D. W. Breck, published in 1973 by John Wiley & Sons, the complete disclosure of which is incorporated herein by specific reference. The three synthetic forms reported by Breck are Zeolite "K-G", described in J. Chem. Soc., p. 2822 (1956), Barrer et al; Zeolite D, described in British Patent No. 868,846 (1961); and Zeolite R, described in U.S. Pat. No. 3,030,181 (1962). Zeolite K-G zeolite has a silica:alumina mole ratio of 2.3:1 to 4.15:1, whereas zeolites D and R have silica:alumina mole ratios of 4.5:1 to 4.9:1 and 3.45:1 to 3.65:1, respectively.

In U.S. Pat. No. 4,440,871, the synthesis of a wide variety of SAPO materials of various framework types is described with a number of specific examples. Also disclosed are a large number of possible organic templates, with some specific examples. In the specific examples a number of CHA framework type materials are described. The preparation of SAPO-34 is reported, using tetraethylammonium hydroxide (TEAOH), or isopropylamine, or mixtures of TEAOH and dipropylamine (DPA) as templates. Also disclosed is a specific example that utilizes cyclohexylamine in the preparation of SAPO-44. Although other template materials are described, there are no other templates indicated as being suitable for preparing SAPO's of the CHA framework type.

U.S. Pat. No. 6,162,415 discloses the synthesis of a silicoaluminophosphate molecular sieve, SAPO-44, which has a CHA framework type in the presence of a directing agent comprising cyclohexylamine or a cyclohexylammonium salt, such as cyclohexylammonium chloride or cyclohexylammonium bromide.

Silicoaluminophosphates of the CHA framework type with low silicon contents are particularly desirable for use in the methanol-to-olefins process. Thus, Wilson, et al., *Microporous and Mesoporous Materials*, 29, 117-126, 1999 report that it is beneficial to have lower Si content for methanol-to-olefins reaction, in particular because low Si content has the effect of reducing propane formation and decreasing catalyst deactivation.

U.S. Pat. No. 6,620,983 discloses a method for preparing silicoaluminophosphate molecular sieves, and in particular low silica silicoaluminophosphate molecular sieve having a Si/Al atomic ratio of less than 0.5, which process comprises forming a reaction mixture comprising a source of aluminum, a source of silicon, a source of phosphorus, at least one organic template, at least one compound which comprises two or more fluorine substituents and capable of providing fluoride ions, and inducing crystallization of the silicoaluminophosphate molecular sieve from the reaction mixture. Suitable organic templates are said to include one or more of tetraethyl ammonium hydroxide, tetraethyl ammonium phosphate, tetraethyl ammonium fluoride, tetraethyl ammonium bromide, tetraethyl ammonium chloride, tetraethyl ammonium acetate, dipropylamine, isopropylamine, cyclohexylamine, morpholine, methylbutylamine, morpholine, diethanolamine, and triethylamine. In the Examples, crystallization is conducted by heating the reaction mixture to 170° C. over 18 hours and then holding the mixture at this temperature for 18 hours to 4 days.

U.S. Pat. No. 6,793,901 discloses a method for preparing a microporous silicoaluminophosphate molecular sieve having the CHA framework type, which process comprises (a) forming a reaction mixture comprising a source of aluminum, a source of silicon, a source of phosphorus, optionally at least one source of fluoride ions and at least one template containing one or more N,N-dimethylamino moieties, (b) inducing crystallization of the silicoaluminophosphate molecular sieve from the reaction mixture, and (c) recovering silicoaluminophosphate molecular sieve from the reaction mixture. Suitable templates are said to include one or more of N,N-dimethylethanolamine, N,N-dimethylbutanolamine, N,N-dimethylheptanolamine, N,N-dimethylhexanolamine, N,N-dimethylethylenediamine, N,N-dimethylpropylenediamine, N,N-dimethylbutylene-diamine, N,N-dimethylheptylenediamine, N,N-dimethylhexylenediamine, or dimethyl-ethylamine, dimethylpropylamine, dimethyl-heptylamine, and dimethylhexylamine. When conducted in the presence of fluoride ions, the synthesis is effective in producing low silica silicoaluminophosphate molecular sieves having a Si/Al atomic ratio of from 0.01 to 0.1. In the Examples, crystallization is conducted by heating the reaction mixture to 170 to 180° C. for 1 to 5 days.

U.S. Pat. No. 6,835,363 discloses a process for preparing microporous crystalline silicoaluminophosphate molecular sieves of CHA framework type, the process comprising: (a) providing a reaction mixture comprising a source of alumina, a source of phosphate, a source of silica, hydrogen fluoride and an organic template comprising one or more compounds of formula (I):

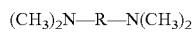

(CH$_3$)$_2$N—R—N(CH$_3$)$_2$ where R is an alkyl radical of from 1 to 12 carbon atoms; (b) inducing crystallization of silicoaluminophosphate from the reaction mixture; and (c) recovering silicoaluminophosphate molecular sieve. Suitable templates are said to include one or more of the group consisting of: N,N,N',N'-tetramethyl-1,3-propane-diamine, N,N,N',N'-tetramethyl-1,4-butanediamine, N,N,N',N'-tetramethyl-1,3-butanediamine, N,N,N',N'-tetramethyl-1,5-pentanediamine, N,N,N',N'-tetramethyl-1,6-hexanediamine, N,N,N',N'-tetramethyl-1,7-heptanediamine, N,N,N',N'-tetramethyl-1,8-octanediamine, N,N,N',N'-tetramethyl-1,9-nonanediamine N,N,N',N'-tetramethyl-1,10-decanediamine, N,N,N',N'-tetramethyl-1,1'-undecanediamine and N,N,N',N'-tetramethyl-1,12-dodecanediamine. In the Examples, crystallization is conducted by heating the reaction mixture to 120 to 200° C. for 4 to 48 hours.

U.S. Pat. No. 7,247,287 discloses the synthesis of silicoaluminophosphate molecular sieves having the CHA framework type employing a directing agent having the formula:

R$^1$R$^2$N—R$^3$ wherein R$^1$ and R$^2$ are independently selected from the group consisting of alkyl groups having from 1 to 3 carbon atoms and hydroxyalkyl groups having from 1 to 3 carbon atoms and R$^3$ is selected from the group consisting of 4- to 8-membered cycloalkyl groups, optionally substituted by 1 to 3 alkyl groups having from 1 to 3 carbon atoms; and 4- to 8-membered heterocyclic groups having from 1 to 3 heteroatoms, said heterocyclic groups being optionally substituted by 1 to 3 alkyl groups having from 1 to 3 carbon atoms and the heteroatoms in said heterocyclic groups being selected from the group consisting of O, N, and S. Preferably, the directing agent is selected from N,N-dimethylcyclohexylamine, N,N-dimethyl-methylcyclohexylamine, N,N-dimethyl-cyclopentylamine, N,N-dimethyl-methyl-cyclopentylamine, N,N-dimethylcycloheptyl-amine, N,N-dimethyl-methylcycloheptylamine, and most preferably is N,N-dimethyl-cyclohexylamine. The synthesis can be effected with or without the presence of fluoride ions and, in the Examples, crystallization is conducted by heating the reaction mixture to 180° C. for 3 to 7 days.

When any molecular sieve is used as an oxygenate conversion catalyst, three of the main economic drivers in evaluating the efficiency and precision of the manufacturing process are the yield of the molecular sieve catalyst, the template efficiency, and the accuracy to which the acid site density of the molecular sieve product can be controlled from the component ingredients. In practice, even small changes in yield, template efficiency, and/or acid site density can have an enormous effect on the economics of a commercial process, and hence there is a continuing need to develop catalysts with improved yields, improved template efficiencies, and/or improved accuracy of acid site densities for use in oxygenate conversion.

According to one aspect of the present invention, it has unexpectedly been found that the prime olefin selectivity (POS or total selectivity to ethylene and propylene in the product) in oxygenate conversion of CHA framework-containing aluminophosphate and silicoaluminophosphate molecular sieves can be enhanced by increasing the crystallization heating rate and optionally (but preferably) by increasing the crystallization time used in their synthesis. This finding is unexpected since the results obtained with CHA framework type molecular sieves produced with slower heating rates or shorter crystallization times tended to produce materials with inferior POS and/or prime olefin ratio (POR or ethylene yield divided by propylene yield) in oxygenate conversion.

According to another aspect of the present invention, it has unexpectedly been found that the POS in oxygenate conversion of CHA framework-containing aluminophosphate and silicoaluminophosphate molecular sieves can be enhanced by reducing the heat-up rate to the crystallization temperature and by shortening the crystallization time used in their synthesis. This finding is unexpected since the results obtained with CHA molecular sieves produced with slower heating rates and longer crystallization times or with faster heating rates and shorter crystallization times tended to produce materials with inferior POS and/or POR in oxygenate conversion.

SUMMARY OF THE INVENTION

In a first aspect, the invention relates to a method of preparing a silicoaluminophosphate molecular sieve having a desired crystal size, the method comprising: (a) providing a synthesis mixture comprising a source of aluminum, a source of phosphorus, a source of silicon, and at least one organic template containing (i) a 4- to 8-membered cycloalkyl group, optionally substituted by 1-3 alkyl groups having from 1-3 carbon atoms, or (ii) a 4- to 8-membered heterocyclic group having from 1-3 heteroatoms, said heterocyclic group being optionally substituted by 1-3 alkyl groups having from 1-3 carbon atoms, and said heteroatoms in said heterocyclic groups being selected from the group consisting of O, N, and S, wherein the synthesis mixture exhibits a Si/Al$_2$ ratio less than 0.33; (b) inducing crystallization of a silicoaluminophosphate molecular sieve, which exhibits 90% or greater CHA framework type character, from said synthesis mixture by heating said synthesis mixture at a heating rate of more than 10° C./hr to a crystallization temperature; (c) crystallizing said silicoaluminophosphate molecular sieve at the crystallization temperature for between 16 hours and 350 hours, such that a yield of silicoaluminophosphate molecular sieve greater than 8.0% is attained, wherein the crystallized silicoaluminophosphate molecular sieve exhibits a Si/Al$_2$ ratio less than 0.33 and has a crystal size distribution such that its average crystal size is not greater than 1.0 μm.

In a second aspect, the invention relates to a method of converting hydrocarbons into olefins comprising: (1) preparing a silicoaluminophosphate molecular sieve according to a method comprising: (a) providing a synthesis mixture comprising a source of aluminum, a source of phosphorus, a source of silicon, and at least one organic template containing (i) a 4- to 8-membered cycloalkyl group, optionally substituted by 1-3 alkyl groups having from 1-3 carbon atoms, or (ii) a 4- to 8-membered heterocyclic group having from 1-3 heteroatoms, said heterocyclic group being optionally substituted by 1-3 alkyl groups having from 1-3 carbon atoms, and said heteroatoms in said heterocyclic groups being selected from the group consisting of O, N, and S, (b) inducing crystallization of a silicoaluminophosphate molecular sieve, which exhibits 90% or greater CHA framework type character, from said synthesis mixture by heating said synthesis mixture at a heating rate of more than 10° C./hr to a crystallization temperature; and (c) crystallizing said silicoaluminophosphate molecular sieve at the crystallization temperature for between 16 hours and 350 hours, such that a yield of silicoaluminophosphate molecular sieve greater than 8.0% is attained, wherein the crystallized silicoaluminophosphate molecular sieve and the synthesis mixture both exhibit a $Si/Al_2$ ratio less than 0.33 and the crystallized silicoaluminophosphate molecular sieve has a crystal size distribution such that its average crystal size is not greater than 3.0 μm; (2) formulating said silicoaluminophosphate molecular sieve, along with a binder and optionally a matrix material, into a silicoaluminophosphate molecular sieve catalyst composition comprising from at least 10% to about 50% molecular sieve; and (c) contacting said catalyst composition with a hydrocarbon feed under conditions sufficient to convert said hydrocarbon feed into a product comprising predominantly one or more olefins to attain a first prime olefin selectivity of at least 70 wt %, wherein the first prime olefin selectivity is at least 1.5 wt % greater than a second prime olefin selectivity that would be attained by preparing a comparable silicoaluminophosphate molecular sieve (i) having a crystal size distribution, based on the crystallized silicoaluminophosphate molecular sieve, such that its average crystal size is greater than 3.0 μm, (ii) made by heating at a rate no more than 5° C./hr up to the crystallization temperature during the step of inducing crystallization, or (iii) both (i) and (ii).

In a third aspect, the invention relates to a method of forming an olefin-based polymer product comprising: (a) preparing a product comprising predominantly one or more olefins according to the method of the second aspect of the invention; and (b) polymerizing at least one of the one or more olefins, optionally with one or more other comonomers and optionally in the presence of a polymerization catalyst, under conditions sufficient to form an olefin-based (co)polymer.

A fourth aspect of the invention relates to a method of converting hydrocarbons into olefins comprising: (1) preparing a silicoaluminophosphate molecular sieve by a method comprising (a) preparing a reaction mixture comprising a source of aluminum, a source of phosphorus, a source of silicon, and at least one organic template containing (i) a 4- to 8-membered cycloalkyl group, optionally substituted by 1-3 alkyl groups having from 1-3 carbon atoms, or (ii) a 4- to 8-membered heterocyclic group having from 1-3 heteroatoms, said heterocyclic group being optionally substituted by 1-3 alkyl groups having from 1-3 carbon atoms, and said heteroatoms in said heterocyclic groups being selected from the group consisting of O, N, and S, (b) heating said reaction mixture at a rate of less than 10° C./hour to a crystallization temperature within the range of about 150° C. to about 225° C., (c) retaining said reaction mixture within said crystallization temperature range for a period of less than 10 hours to induce crystallization of a silicoaluminophosphate molecular sieve, and (d) recovering a crystallized silicoaluminophosphate molecular sieve from the reaction mixture; (2) formulating said silicoaluminophosphate molecular sieve, along with a binder and optionally a matrix material, into a silicoaluminophosphate molecular sieve catalyst composition comprising from at least 10% to about 50% molecular sieve; and (3) contacting said catalyst composition with a hydrocarbon feed under conditions sufficient to convert said hydrocarbon feed into a product comprising predominantly one or more olefins to attain a first prime olefin selectivity of at least 76 wt %, wherein the first prime olefin selectivity is at least 3.0 wt % greater than a second prime olefin selectivity that would be attained by contacting the hydrocarbon feed under similar conditions with a comparable silicoaluminophosphate molecular sieve made by heating the reaction mixture at a rate of at least 20° C./hr up to the crystallization temperature.

A fifth aspect of the invention relates to a method of forming an olefin-based polymer product comprising: (1) preparing a product comprising predominantly one or more olefins according to the fourth aspect of the invention; and (2) polymerizing at least one of the one or more olefins, optionally with one or more other comonomers and optionally in the presence of a polymerization catalyst, under conditions sufficient to form an olefin-based (co)polymer.

DETAILED DESCRIPTION OF THE EMBODIMENTS

Figure 1:
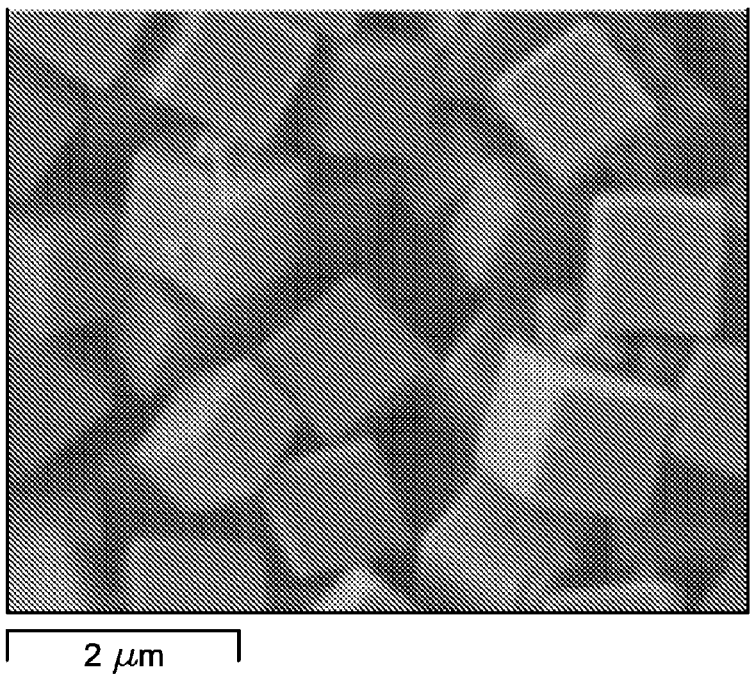
FIG. 1 shows an SEM micrograph of a molecular sieve made according to Comparative Example A.
Figure 2:
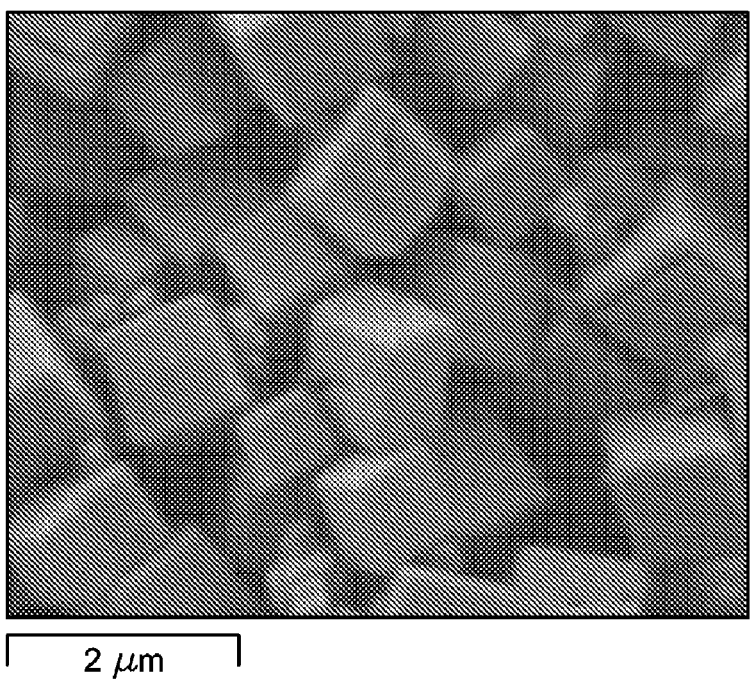
FIG. 2 shows an SEM micrograph of a molecular sieve made according to Comparative Example B.
Figure 3:
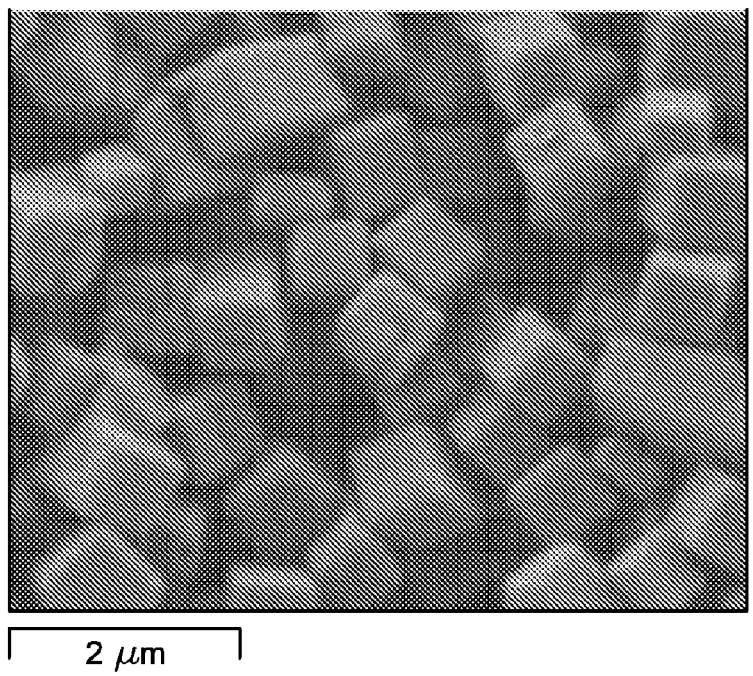
FIG. 3 shows an SEM micrograph of a molecular sieve made according to Comparative Example C.
Figure 4:
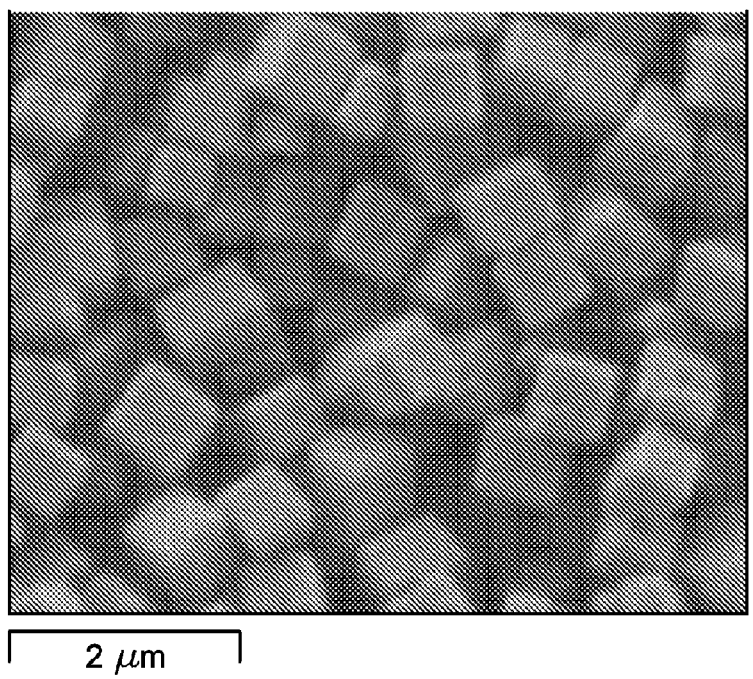
FIG. 4 shows an SEM micrograph of a molecular sieve made according to Comparative Example D.
Figure 5:
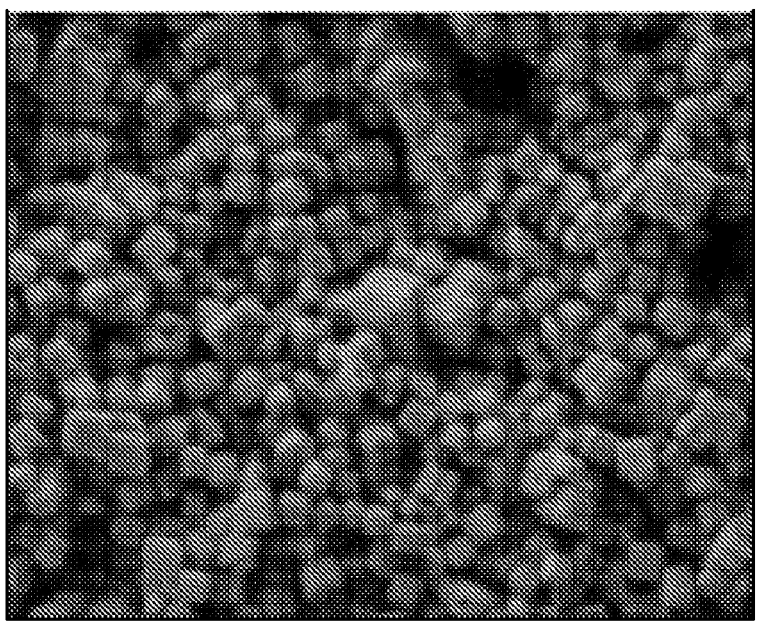
FIG. 5 shows an SEM micrograph of a molecular sieve made according to Example 1.
Figure 6:
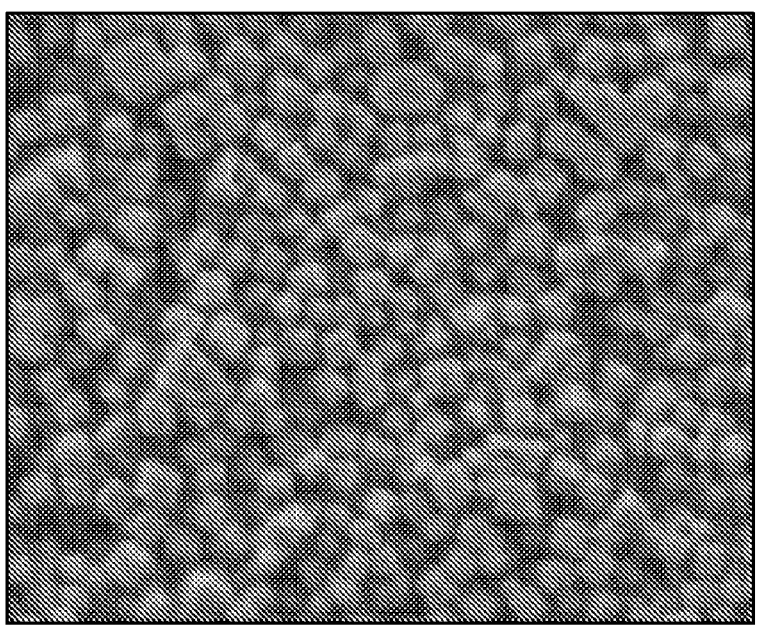
FIG. 6 shows an SEM micrograph of a molecular sieve made according to Example 2.
Figure 7:
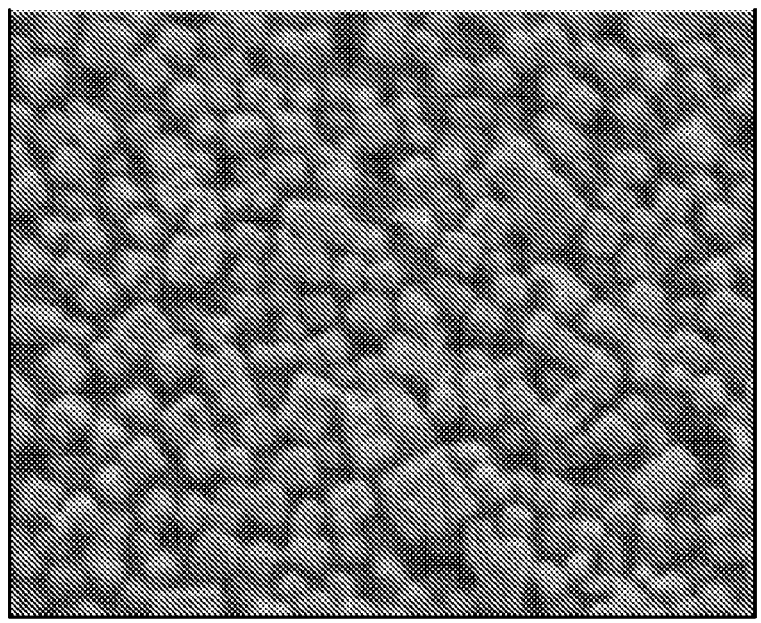
FIG. 7 shows an SEM micrograph of a molecular sieve made according to Example 3.
Figure 8:
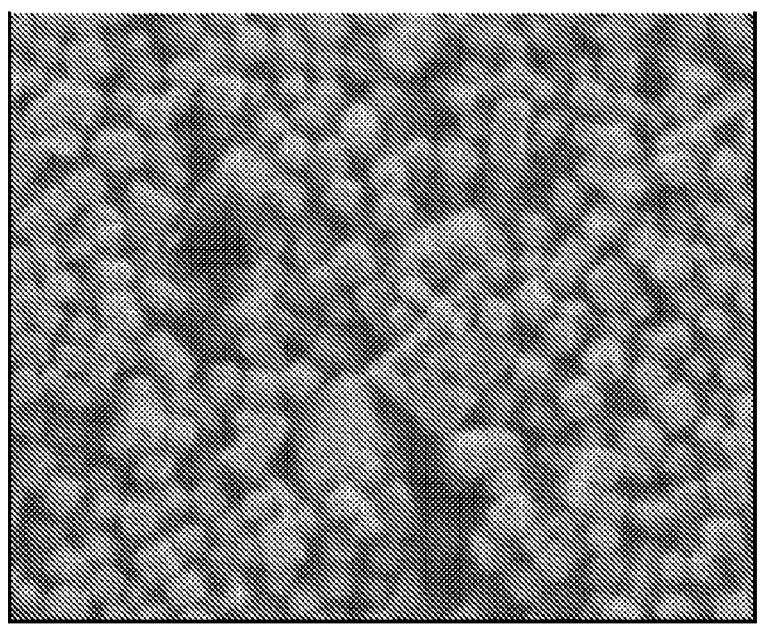
FIG. 8 shows an SEM micrograph of a molecular sieve made according to Example 4.

Described herein is a method of synthesizing a crystalline aluminophosphate or silicoaluminophosphate containing a CHA framework type molecular sieve and to the use of the resultant molecular sieve as a catalyst in organic conversion reactions, especially the conversion of oxygenates to light olefins.

In the first aspect in particular, it has been found that, by employing a relatively fast heat-up rate (typically, though not necessarily at relatively long crystallization times) in the molecular sieve synthesis, it is possible to produce a CHA framework-type containing molecular sieve with improved POS and/or POR in oxygenate conversion.

In the fourth aspect in particular, it has been found that by employing a relatively slow heat-up rate and relatively short crystallization times in the molecular sieve synthesis, it is possible to produce a CHA framework-type containing molecular sieve with improved POS and/or POR in oxygenate conversion.

In the present method, a reaction mixture is prepared comprising a source of aluminum, a source of phosphorous, at least one organic directing agent, and, optionally, a source of silicon. Any organic directing agent capable of directing the synthesis of CHA framework type molecular sieves can be employed, but generally the directing agent is a compound having the formula (I):

$$R^1R^2N\text{—}R^3 \qquad (I)$$

wherein $R^1$ and $R^2$ are independently selected from the group consisting of alkyl groups having from 1 to 3 carbon atoms and hydroxyalkyl groups having from 1 to 3 carbon atoms and $R^3$ is selected from the group consisting of 4- to 8-membered cycloalkyl groups, optionally substituted by 1 to 3 alkyl groups having from 1 to 3 carbon atoms; and 4- to 8-membered heterocyclic groups having from 1 to 3 heteroatoms, said heterocyclic groups being optionally substituted by 1 to 3 alkyl groups having from 1 to 3 carbon atoms and the heteroatoms in said heterocyclic groups being selected from the group consisting of O, N, and S.

More particularly, the organic directing agent is a compound having the formula (II):

$$(CH_3)_2N\text{—}R^3 \qquad (II)$$

wherein $R^3$ is a 4- to 8-membered cycloalkyl group, especially a cyclohexyl group, optionally substituted by 1 to 3 methyl groups. Particular examples of suitable organic directing agents include, but are not limited to, at least one of N,N-dimethyl-cyclohexylamine, N,N-dimethyl-methylcyclohexylamine, N,N-dimethyl-cyclopentylamine, N,N-dimethyl-methylcyclopentylamine, N,N-dimethyl-cycloheptylamine, and N,N-dimethyl-methylcycloheptylamine, especially N,N-dimethyl-cyclohexylamine.

The sources of aluminum, phosphorus, and silicon suitable for use in the present synthesis method are typically those known in the art or as described in the literature for the production of aluminophosphates and silicoaluminophosphates. For example, the aluminum source may be an aluminum oxide (alumina), optionally hydrated, an aluminum salt, especially a phosphate, an aluminate, or a mixture thereof. Other sources may include alumina sols or organic alumina sources, e.g., aluminum alkoxides such as aluminum isopropoxide. A preferred source is a hydrated alumina, most preferably pseudoboehmite, which contains about 75% $Al_2O_3$ and 25% $H_2O$ by weight. Typically, the source of phosphorus is a phosphoric acid, especially orthophosphoric acid, although other phosphorus sources, for example, organophosphates (e.g. trialkylphosphates such as triethylphosphate) and aluminophosphates may be used. When organophosphates and/or aluminophosphates are used, typically they are present collectively in a minor amount (i.e., less than 50% by weight of the phosphorus source) in combination with a majority (i.e., at least 50% by weight of the phosphorus source) of an inorganic phosphorus source (such as phosphoric acid). Suitable sources of silicon include silica, for example colloidal silica and fumed silica, as well as organic silicon source, e.g. a tetraalkyl orthosilicate.

Although, in most embodiments, the sources of silicon, phosphorus, and aluminum are the only components that form the framework of a calcined silicoaluminophosphate molecular sieve according to the invention, it is possible for some small portion (e.g., typically no more than about 10 wt %, preferably no more than about 5 wt %) of the silicon source can be substituted with a source of one or more of magnesium, zinc, iron, cobalt, nickel, manganese, and chromium.

In some embodiments, the reaction mixture can have a molar composition within the following ranges:
$P_2O_5:Al_2O_3$ from about 0.75 to about 1.25,
$SiO_2:Al_2O_3$ from about 0.01 to about 0.32,
$H_2O:Al_2O_3$ from about 25 to about 50, and
$SDA:Al_2O_3$ from about 1 to about 3,
where SDA designates the structure directing agent (template), and wherein the molar ratios for the aluminum, phosphorus, and silicon sources are calculated based on the oxide forms, regardless of the form of the source added to the reaction mixture (e.g., whether the phosphorus source is added to the reaction mixture as phosphoric acid, $H_3PO_4$, or as triethylphosphate, the molar ratio is normalized to $P_2O_5$ molar equivalents).

Although the reaction mixture may also contain a source of fluoride ions, it is found that the present synthesis will proceed in the absence of fluoride ions and hence it is generally preferred to employ a reaction mixture which is substantially free of fluoride ions.

Typically, the reaction mixture also contains seeds to facilitate the crystallization process. The amount of seeds employed can vary widely, but generally the reaction mixture comprises from about 0.01 ppm by weight to about 10,000 ppm by weight, such as from about 100 ppm by weight to about 5,000 by weight, of said seeds. Generally, the seeds can be homostructural with the desired product, that is are of a CHA framework type material, although heterostructural seeds of, for example, an AEI, LEV, ERI, AFX, or OFF framework-type molecular sieve, or a combination or intergrowth thereof, may be used. The seeds may be added to the reaction mixture as a suspension in a liquid medium, such as water; in some cases, particularly where the seeds are of relatively small size, the suspension can be colloidal. The production of colloidal seed suspensions and their use in the synthesis of molecular sieves are disclosed in, for example, International Publication Nos. WO 00/06493 and WO 00/06494, both published on Feb. 10, 2000 and both of which are incorporated herein by reference.

In the first aspect of the invention, crystallization of the reaction mixture is carried out at either static or stirred conditions in a suitable reactor vessel, such as for example, polypropylene jars or Teflon-lined or stainless steel autoclaves. In one embodiment, the crystallization regime can involve heating the reaction mixture relatively quickly, at a rate of more than 10° C./hour, conveniently at least 15° C./hour or at least 20° C./hour, for example from about 15° C./hour to about 150° C./hour or from about 20° C./hour to about 100° C./hour, to the desired crystallization temperature, typically between about 50° C. and about 250° C., for example from about 150° C. to about 225° C. or from about 150° C. to about 200° C., such as from about 160° C. to about 195° C. In some embodiments, however, the desired crystallization temperature is additionally at least 165° C., for example at least 170° C., and can optionally also be not more than 190° C., for example not more than 185° C. or not more than 180° C. In any of these embodiments, when the desired crystallization temperature is reached, the crystallization can be terminated immediately or from about 5 minutes to about 350 hours, and the reaction mixture can be allowed to cool;

additionally or alternatively, the crystallization can run for at least about 12 hours, preferably at least about 16 hours, for example at least 24 hours, at least 36 hours, at least 48 hours, at least 60 hours, at least 72 hours, at least 84 hours, at least 96 hours, at least 120 hours, or at least 144 hours before cooling. Additionally in this embodiment, on cooling, the crystalline product can be recovered by standard means, such as by centrifugation or filtration, then washed and dried. Optionally, the step of inducing crystallization can be done while stirring.

In the fourth aspect of the invention, crystallization of the reaction mixture is carried out at either static or stirred conditions in a suitable reactor vessel, such as for example, polypropylene jars or Teflon-lined or stainless steel autoclaves. In one embodiment, the crystallization regime can involve heating the reaction mixture slowly, at a rate of less than 8° C./hour, conveniently at least 1° C./hour, such as from about 2° C./hour to about 6° C./hour, to the desired crystallization temperature, typically between about 50° C. and about 250° C., for example from about 150° C. to about 225° C. or from about 150° C. to about 200° C., such as from about 160° C. to about 195° C. In some embodiments, however, the desired crystallization temperature is additionally at least 165° C., for example at least 170° C., and can optionally also be not more than 190° C., for example not more than 185° C. or not more than 180° C. In any of these embodiments, when the desired crystallization temperature is reached, the crystallization can be terminated immediately (though, in some embodiments, about 5 minutes will pass) or at least within less than 10 hours, such as less than 5 hours, and the reaction mixture can be allowed to cool. Additionally in this embodiment, on cooling, the crystalline product can be recovered by standard means, such as by centrifugation or filtration, then washed and dried. Optionally, the step of inducing crystallization can be done while stirring.

In one embodiment of the first aspect of the invention, the crystallized silicoaluminophosphate molecular sieve has a crystal size distribution such that its average crystal size is less than 1.1 µm, preferably no more than 1.0 µm, for example no more than 0.9 µm, no more than 0.8 µm, or no more than 0.7 µm. In one embodiment of the second and/or third aspect(s) of the invention, the crystallized silicoaluminophosphate molecular sieve has a crystal size distribution such that its average crystal size is less than 3.5 µm, preferably no more than 3.0 µm, for example no more than 2.5 µm, no more than 2.0 µm, no more than 1.5 µm, no more than 1.2 µm, no more than 1.1 µm, no more than 1.0 µm, no more than 0.9 µm, no more than 0.8 µm, or no more than 0.7 µm. In one embodiment of the fourth aspect of the invention, the crystallized silicoaluminophosphate molecular sieve has a crystal size distribution such that its average crystal size is less than 1.5 µm, preferably no more than 1.2 µm, for example no more than 1.1 µm, no more than 1.0 µm, or no more than 0.9 µm.

As used herein, the term "average crystal size," in reference to a crystal size distribution, should be understood to refer to a measurement on a representative sample or an average of multiple samples that together form a representative sample. Average crystal size can be measured by SEM, in which case the crystal size of at least 30 crystals must be measured in order to obtain an average crystal size, and/or average crystal size can be measured by a laser light scattering particle size analyzer instrument, in which case the measured $d_{50}$ of the sample(s) can represent the average crystal size. It should also be understood that, while many of the crystals dealt with herein are relatively uniform (for instance, very close to cubic, thus having little difference between diameter measured along length, height, or width, e.g. when viewed in an SEM), the "average crystal size," when measured visually by SEM, represents the longest distance along one of the three-dimensional orthogonal axes (e.g., longest of length, width/diameter, and height, but not diagonal, in a cube, rectangle, parallelogram, ellipse, cylinder, frusto-cone, platelet, spheroid, or rhombus, or the like). However, the $d_{50}$, when measured by light scattering in a particle size analyzer, is reported as a spherical equivalent diameter, regardless of the shape and/or relative uniformity of shape of the crystals in each sample. In certain circumstances, the $d_{50}$ values measured by the particle size analyzer may not correspond, even roughly, to the average crystal size measured visually by a representative SEM micrograph. Often in these cases, the discrepancy relates to an agglomeration of relatively small crystals that the particle size analyzer interprets as a single particle. In such circumstances, where the $d_{50}$ values from the particle size analyzer and the average crystal size from a representative SEM are significantly different, the representative SEM micrograph should be the more accurate measure of "average crystal size."

In a preferred embodiment, the order of addition of the components in the mixture (i.e., in step (a)) can be important and can advantageously be tailored, e.g. to provide better homogeneity. For instance, step (a) can preferably comprise: (i) combining the source of phosphorus and the source of aluminum, optionally with a liquid mixture medium, to form a primary mixture; (ii) aging the primary mixture for an aging time and under aging conditions (e.g., at an aging temperature), preferably sufficient to allow homogenization of the primary mixture, physico-chemical interaction between the source of phosphorus and the source of aluminum, or both; and (iii) adding the source of silicon, the at least one organic template, and optionally additional liquid mixture medium, to the aged primary mixture to form the synthesis mixture. In certain cases of this embodiment, within step (iii), said source of silicon is combined with said primary mixture prior to adding said at least one organic template (structure directing agent, or SDA). Advantageously, said primary mixture and said source of silicon can be combined to form a secondary mixture for a time and under conditions (e.g., temperature), preferably sufficient to allow homogenization of the secondary mixture, physico-chemical interaction between said source of silicon and said primary mixture, or both, after which said at least one organic template is combined therewith.

When a component is added to a mixture to allow homogenization and/or physico-chemical interaction, the aging time and temperature are two of the primary conditions. Although a variety of conditions can exist to allow sufficient contact for homogenization and/or interaction, in one embodiment, when the aging temperature is somewhere between 0° C. and 50° C., the aging time can advantageously be at least 5 minutes, for example at least 10 minutes, at least 15 minutes, at least 20 minutes, at least 25 minutes, at least 30 minutes, at least 45 minutes, at least 1 hour, or at least 2 hours. Again, when the aging temperature is somewhere between 0° C. and 50° C., the aging time does not really have a maximum, but can be up to 350 hours, for example up to 300 hours, up to 250 hours, up to 200 hours, up to 168 hours, up to 96 hours, up to 48 hours, up to 24 hours, up to 16 hours, up to 12 hours, up to 8 hours, up to 6 hours, or up to 4 hours, depending on practical concerns relating to synthesis timing, cost efficiency, manufacture schedules, or the like.

Preferably, the $Si/Al_2$ ratio added to the synthesis mixture can be as close as possible to the $Si/Al_2$ ratio of the crystallized silicoaluminophosphate molecular sieve (e.g. difference between the $Si/Al_2$ ratio in the synthesis mixture and in the crystallized silicoaluminophosphate molecular sieve can be no more than 0.10, preferably no more than 0.08, for example no more than 0.07) and/or the synthesis mixture and the crystallized silicoaluminophosphate molecular sieve can both exhibit a relatively low $Si/Al_2$ ratio (e.g., both can be less than 0.33, preferably less than 0.30, for example no more than 0.25, no more than 0.20, no more than 0.15, or no more than 0.10).

In a preferred embodiment, one or more of the following are satisfied: the source of aluminum comprises alumina; the source of phosphorus comprises phosphoric acid; the source of silicon can include an organosilicate comprising a tetraalkylorthosilicate; and the at least one organic template comprises N,N-dimethylcyclohexylamine.

The product of the crystallization is an aluminophosphate or silicoaluminophosphate containing a CHA framework-type molecular sieve having an X-ray diffraction pattern including at least the d-spacings shown in Table 1 below:

TABLE 1

| d (A) | Relative Intensities I/Io (%) |
|---|---|
| 9.26 | 100 |
| 6.30 | 20 |
| 5.64 | 15 |
| 5.51 | 57 |
| 4.96 | 25 |
| 4.92 | 27 |
| 4.29 | 76 |
| 4.18 | 21 |
| 3.55 | 32 |
| 3.50 | 20 |
| 3.42 | 10 |
| 2.91 | 22 |
| 2.88 | 26 |
| 2.87 | 19 |

Although the crystallization product is normally a single phase CHA framework-type molecular sieve, in some cases the product may contain an intergrowth of a CHA framework-type molecular sieve with, for example an AEI framework-type molecular sieve or small amounts of other crystalline phases, such as APC and/or AFI framework-type molecular sieves. In one embodiment, it is preferable for the crystallization product to have as high an amount of CHA framework type as possible, e.g., at least 95% CHA framework-type character, or even about 100% CHA framework-type character (or as close as possible to single phase CHA framework-type character as can currently be measured). Without being bound by theory, it is believed that silicoaluminophosphate molecular sieves having increased CHA framework-type character (and/or increased uniformity of distribution of silicon within the molecular sieve framework structure, i.e., decreased amounts of silicon islanding) can advantageously exhibit better performance (e.g., increased POS and optionally also POR) in oxygenates-to-olefins conversion reactions, particularly in methanol-to-olefins conversion reactions.

As a result of the crystallization process, the recovered crystalline product contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system.

Once the crystalline product has been activated, it can be formulated into a catalyst composition by combination with other materials, such as binders and/or matrix materials, which provide additional hardness or catalytic activity to the finished catalyst.

Materials which can be blended with the present molecular sieve material include a large variety of inert and catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of present CHA-containing crystalline material contained in the final catalyst product ranges from 10 to 90 weight percent of the total catalyst, preferably 20 to 80 weight percent of the total catalyst.

The CHA framework type crystalline material produced by the present process can be used to dry gases and liquids; for selective molecular separation based on size and polar properties; as an ion-exchanger; as a chemical carrier; in gas chromatography; and as a catalyst in organic conversion reactions. Examples of suitable catalytic uses of the CHA framework type crystalline material described herein include (a) hydrocracking of heavy petroleum residual feedstocks, cyclic stocks and other hydrocrackate charge stocks, normally in the presence of a hydrogenation component selected from Groups 6 and 8-10 of the Periodic Table of Elements; (b) dewaxing, including isomerization dewaxing, to selectively remove straight chain paraffins from hydrocarbon feedstocks typically boiling above 177° C., including raffinates and lubricating oil basestocks; (c) catalytic cracking of hydrocarbon feedstocks, such as naphthas, gas oils, and residual oils, normally in the presence of a large pore cracking catalyst, such as zeolite Y; (d) oligomerization of straight and branched chain olefins having from 2-21, preferably 2-5, carbon atoms, to produce medium to heavy olefins which are useful for both fuels, e.g., gasoline or a gasoline blending stock, and chemicals; (e) isomerization of olefins, particularly olefins having 4-6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene, to produce alkylated aromatics, such as ethylbenzene and cumene; (i) isomerization of dialkylaromatic hydrocarbons, such as xylenes; (j) catalytic reduction of nitrogen oxides; and (k) synthesis of monoalkylamines and dialkylamines.

In particular, the CHA framework type crystalline material produced by the present process is useful as a catalyst in the conversion of oxygenates to one or more olefins, particularly ethylene and propylene. As used herein, the term "oxygenates" is defined to include, but is not necessarily limited to, aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from 1-10 carbon atoms, such as from 1-4 carbon atoms.

Representative oxygenates include lower straight chain or branched aliphatic alcohols, their unsaturated counterparts, and their nitrogen, halogen, and sulfur analogues. Examples of suitable oxygenate compounds can include, but are not necessarily limited to: methanol; ethanol; n-propanol; isopropanol; $C_4$ to $C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines; n-alkyl halides; n-alkyl sulfides having n-alkyl groups comprising from 3-10 carbon atoms; and the like; and mixtures thereof. Particularly suitable oxygenate compounds are methanol, dimethyl ether, and mixtures thereof, and most preferably comprise methanol. As used herein, the term "oxygenate" designates only the organic material used as the feed. The total charge of feed to the reaction zone may contain additional compounds, such as diluents.

In one embodiment of the oxygenate conversion process, a feedstock comprising an organic oxygenate, optionally with one or more diluents, is contacted in the vapor phase in a reaction zone with a catalyst comprising the present molecular sieve at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is(are) generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents include water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including but not limited to autogenous pressures and pressures in the range from about 0.1 kPa to about 10 MPa. Conveniently, the pressure can be in the range from about 7 kPa to about 5 MPa, such as from about 50 kPa to about 1 MPa. The foregoing pressures are exclusive of diluents, if any are present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene and/or propylene still may form.

In a preferred embodiment of the second aspect of the invention, the method of converting hydrocarbons into olefins according to the invention comprises: (1) preparing a silicoaluminophosphate molecular sieve according to the first aspect of the invention and/or a method comprising: (a) providing a synthesis mixture comprising a source of aluminum, a source of phosphorus, a source of silicon, and at least one organic template containing (i) a 4- to 8-membered cycloalkyl group, optionally substituted by 1-3 alkyl groups having from 1-3 carbon atoms, or (ii) a 4- to 8-membered heterocyclic group having from 1-3 heteroatoms, said heterocyclic group being optionally substituted by 1-3 alkyl groups having from 1-3 carbon atoms, and said heteroatoms in said heterocyclic groups being selected from the group consisting of O, N, and S, (b) inducing crystallization of a silicoaluminophosphate molecular sieve, which exhibits 90% or greater CHA framework type character, from said synthesis mixture by heating said synthesis mixture at a heating rate of more than 10° C./hr to a crystallization temperature; and (c) crystallizing said silicoaluminophosphate molecular sieve at the crystallization temperature for between 16 hours and 350 hours, such that a yield of silicoaluminophosphate molecular sieve greater than 8.0% is attained, wherein the crystallized silicoaluminophosphate molecular sieve and the synthesis mixture both exhibit a $Si/Al_2$ ratio less than 0.33 and the crystallized silicoaluminophosphate molecular sieve has a crystal size distribution such that its average crystal size is not greater than 3.0 µm; (2) formulating said silicoaluminophosphate molecular sieve, along with a binder and optionally a matrix material, into a silicoaluminophosphate molecular sieve catalyst composition comprising from at least 10% to about 50% molecular sieve; and (c) contacting said catalyst composition with a hydrocarbon feed under conditions sufficient to convert said hydrocarbon feed into a product comprising predominantly one or more olefins to attain a first prime olefin selectivity of at least 70 wt % (as measured at about 500° C.). Advantageously, in this embodiment, the first prime olefin selectivity can be at least 1.5 wt % greater than a second prime olefin selectivity (also measured at about 500° C.) that would be attained by preparing a comparable silicoaluminophosphate molecular sieve (i) having a crystal size distribution, based on the crystallized silicoaluminophosphate molecular sieve, such that its average crystal size is greater than 3.0 µm, (ii) made by heating at a rate no more than 5° C./hr up to the crystallization temperature during the step of inducing crystallization, (iii) or both (i) and (ii). Preferably, the hydrocarbon feed is an oxygenate-containing feed comprising methanol, dimethylether, or a combination thereof, and the one or more olefins typically comprises ethylene, propylene, or a combination thereof.

In a preferred embodiment of the fourth aspect of the invention, the method of converting hydrocarbons into olefins according to the invention comprises: (a) preparing a silicoaluminophosphate molecular sieve according to the fourth aspect of the invention; (b) formulating said silicoaluminophosphate molecular sieve, along with a binder and optionally a matrix material, into a silicoaluminophosphate molecular sieve catalyst composition, typically comprising from at least 10% to about 50% molecular sieve; and (c) contacting said catalyst composition with a hydrocarbon feed under conditions sufficient to convert said hydrocarbon feed into a product comprising predominantly one or more olefins, preferably to attain a first prime olefin selectivity of at least 76 wt % (as measured at about 525° C.). Advantageously, in this embodiment, the first prime olefin selectivity is at least 3.0 wt % greater than a second prime olefin selectivity (also as measured at about 525° C.) that would be attained by contacting the hydrocarbon feed under similar conditions with a comparable silicoaluminophosphate molecular sieve made by heating the reaction mixture at a rate of at least 20° C./hr up to the crystallization temperature. Additionally or alternatively, in this embodiment, when the first and second prime olefin selectivities are measured at about 500° C., the first POS can be at least 75 wt % and also at least 2.0 wt % greater than the second POS. Preferably, the hydrocarbon feed is an oxygenate-containing feed comprising methanol, dimethylether, or a combination thereof, and the one or more olefins typically comprises ethylene, propylene, or a combination thereof.

A wide range of weight hourly space velocities (WHSV) for the feedstock will function in the oxygenate conversion process. WHSV is defined as weight of feed (excluding diluents) per hour per weight of a total reaction volume of molecular sieve catalyst (excluding inert and/or fillers). The WHSV generally should be in the range from about $0.01\ hr^{-1}$ to about $500\ hr^{-1}$, such from about $0.5\ hr^{-1}$ to about $300\ hr^{-1}$, for example from about $0.1\ hr^{-1}$ to about $200\ hr^{-1}$.

A practical embodiment of a reactor system for the oxygenate conversion process is a circulating fluid bed reactor with continuous regeneration. Fixed beds are generally not preferred for the process, because oxygenate-to-olefin conversion is a highly exothermic process that requires several stages with intercoolers or other cooling devices. The reaction also results in a high pressure drop, due to the production of low pressure, low density gas.

Because the catalyst typically needs to be regenerated frequently, the reactor should preferably allow easy removal of at least a portion of the catalyst to a regenerator, where the catalyst can be subjected to a regeneration medium, such as a gas comprising oxygen, for example air, to burn off coke from the catalyst, which should restore at least some of the catalyst activity. The conditions of temperature, oxygen partial pressure, and residence time in the regenerator can typically be selected to achieve a coke content on regenerated catalyst of less than about 1 wt %, for example less than about 0.5 wt %. At least a portion of the regenerated catalyst should be returned to the reactor.

In a preferred embodiment of the third aspect of the invention, the method of forming an olefin-based polymer product comprises: (a) preparing a product comprising predominantly one or more olefins according to the method of the second aspect of the invention; and (b) polymerizing at least one of the one or more olefins, optionally with one or more other comonomers and optionally (but preferably) in the presence of a polymerization catalyst, under conditions sufficient to form an olefin-based (co)polymer.

In a preferred embodiment of the fifth aspect of the invention, the method of forming an olefin-based polymer product comprises: (a) preparing a product comprising predominantly one or more olefins according to the method of the fourth aspect of the invention; and (b) polymerizing at least one of the one or more olefins, optionally with one or more other comonomers and optionally (but preferably) in the presence of a polymerization catalyst, under conditions sufficient to form an olefin-based (co)polymer.

Preferably, in either of the polymer-related aspects of the invention, the hydrocarbon feed can be an oxygenate-containing feed comprising methanol, dimethylether, or a combination thereof, the one or more olefins typically can comprises ethylene, propylene, or a combination thereof, and the olefin-based (co)polymer can be an ethylene-containing (co)polymer, a propylene-containing (co)polymer, or a copolymer, mixture, or blend thereof.

Additionally or alternately, the invention can be described by the following embodiments.

Embodiment 1

A method of preparing a silicoaluminophosphate molecular sieve having a desired crystal size, the method comprising: (a) providing a synthesis mixture comprising a source of aluminum, a source of phosphorus, a source of silicon, and at least one organic template containing (i) a 4- to 8-membered cycloalkyl group, optionally substituted by 1-3 alkyl groups having from 1-3 carbon atoms, or (ii) a 4- to 8-membered heterocyclic group having from 1-3 heteroatoms, said heterocyclic group being optionally substituted by 1-3 alkyl groups having from 1-3 carbon atoms, and said heteroatoms in said heterocyclic groups being selected from the group consisting of O, N, and S, wherein the synthesis mixture exhibits a $Si/Al_2$ ratio less than 0.33; (b) inducing crystallization of a silicoaluminophosphate molecular sieve, which exhibits 90% or greater CHA framework type character, from said synthesis mixture by heating said synthesis mixture at a heating rate of more than 10° C./hr to a crystallization temperature; and (c) crystallizing said silicoaluminophosphate molecular sieve at the crystallization temperature for between 16 hours and 350 hours, such that a yield of silicoaluminophosphate molecular sieve greater than 8.0% is attained, wherein the crystallized silicoaluminophosphate molecular sieve exhibits a $Si/Al_2$ ratio less than 0.33 and has a crystal size distribution such that its average crystal size is not greater than 1.0 μm.

Embodiment 2

A method of converting hydrocarbons into olefins comprising: (1) preparing a silicoaluminophosphate molecular sieve according to a method comprising: (a) providing a synthesis mixture comprising a source of aluminum, a source of phosphorus, a source of silicon, and at least one organic template containing (i) a 4- to 8-membered cycloalkyl group, optionally substituted by 1-3 alkyl groups having from 1-3 carbon atoms, or (ii) a 4- to 8-membered heterocyclic group having from 1-3 heteroatoms, said heterocyclic group being optionally substituted by 1-3 alkyl groups having from 1-3 carbon atoms, and said heteroatoms in said heterocyclic groups being selected from the group consisting of O, N, and S, (b) inducing crystallization of a silicoaluminophosphate molecular sieve, which exhibits 90% or greater CHA framework type character, from said synthesis mixture by heating said synthesis mixture at a heating rate of more than 10° C./hr to a crystallization temperature; and (c) crystallizing said silicoaluminophosphate molecular sieve at the crystallization temperature for between 16 hours and 350 hours, such that a yield of silicoaluminophosphate molecular sieve greater than 8.0% is attained, wherein the crystallized silicoaluminophosphate molecular sieve and the synthesis mixture both exhibit a $Si/Al_2$ ratio less than 0.33 and the crystallized silicoaluminophosphate molecular sieve has a crystal size distribution such that its average crystal size is not greater than 3.0 μm; (2) formulating said silicoaluminophosphate molecular sieve, along with a binder and optionally a matrix material, into a silicoaluminophosphate molecular sieve catalyst composition comprising from at least 10% to about 50% molecular sieve; and (c) contacting said catalyst composition with a hydrocarbon feed under conditions sufficient to convert said hydrocarbon feed into a product comprising predominantly one or more olefins to attain a first prime olefin selectivity of at least 70 wt %, wherein the first prime olefin selectivity is at least 1.5 wt % greater than a second prime olefin selectivity that would be attained by preparing a comparable silicoaluminophosphate molecular sieve (i) having a crystal size distribution, based on the crystallized silicoaluminophosphate molecular sieve, such that its average crystal size is greater than 3.0 μm, (ii) made by heating at a rate no more than 5° C./hr up to the crystallization temperature during the step of inducing crystallization, or (iii) both (i) and (ii).

Embodiment 3

A method of converting hydrocarbons into olefins comprising: (1) preparing a silicoaluminophosphate molecular sieve by a method comprising (a) preparing a reaction mixture comprising a source of aluminum, a source of phosphorus, a source of silicon, and at least one organic template containing (i) a 4- to 8-membered cycloalkyl group, optionally substituted by 1-3 alkyl groups having from 1-3 carbon atoms, or (ii) a 4- to 8-membered heterocyclic group having from 1-3 heteroatoms, said heterocyclic group being optionally substituted by 1-3 alkyl groups having from 1-3 carbon atoms, and said heteroatoms in said heterocyclic groups being selected from the group consisting of O, N, and S, (b) heating said reaction mixture at a rate of less than 10° C./hour to a crystallization temperature within the range of about 150° C. to about 225° C., (c) retaining said reaction mixture within said crystallization temperature range for a period of less than 10 hours to induce crystallization of a silicoaluminophosphate molecular sieve, and (d) recovering a crystallized silicoaluminophosphate molecular sieve from the reaction mixture; (2) formulating said silicoaluminophosphate molecular sieve, along with a binder and optionally a matrix material, into a silicoaluminophosphate molecular sieve catalyst composition comprising from at least 10% to about 50% molecular sieve; and (3) contacting said catalyst composition with a hydrocarbon feed under conditions sufficient to convert said hydrocarbon feed into a product comprising predominantly one or more olefins to attain a first prime olefin selectivity of at least 76 wt %, wherein the first prime olefin selectivity is at least 3.0 wt % greater than a second prime olefin selectivity that would be attained by contacting the hydrocarbon feed under similar conditions with a comparable silicoaluminophosphate molecular sieve made by heating the reaction mixture at a rate of at least 20° C./hr up to the crystallization temperature.

Embodiment 4

The method of any of the previous embodiments, wherein the at least one organic template comprises N,N-dimethylcyclohexylamine.

Embodiment 5

The method of embodiment 1 or embodiment 2, wherein the heating rate in step (b) is more than 20° C./hr.

Embodiment 6

The method of embodiment 1 or embodiment 2, wherein the heating rate in step (b) is between 15° C./hr and 150° C./hr.

Embodiment 7

The method of embodiment 3 or embodiment 4, wherein the heating rate in step (b) is (i) less than 8° C./hour, (ii) at least 1° C./hour, or (iii) both (i) and (ii).

Embodiment 8

The method of any of the previous embodiments, wherein said crystallization temperature is between 150° C. and 200° C.

Embodiment 9

The method of any of the previous embodiments, wherein crystallization is induced while stirring.

Embodiment 10

The method of any of embodiments 1-2, 5-6, and 8-9, wherein the crystallized silicoaluminophosphate molecular sieve from step (c) has a crystal size distribution such that the average crystal size is less than 0.9 μm.

Embodiment 11

The method of any of the previous embodiments, wherein the synthesis mixture and the crystallized silicoaluminophosphate molecular sieve both exhibit a $Si/Al_2$ ratio less than 0.33.

Embodiment 12

The method of any of the previous embodiments, wherein step (a) comprises: (i) combining the source of phosphorus and the source of aluminum, optionally with a liquid mixture medium, to form a primary mixture; (ii) aging the primary mixture for an aging time and under aging conditions sufficient to allow homogenization of the primary mixture, physico-chemical interaction between the source of phosphorus and the source of aluminum, or both; and (iii) adding the source of silicon, the at least one organic template, and optionally additional liquid mixture medium, to the aged primary mixture to form the synthesis mixture.

Embodiment 13

The method of embodiment 12, wherein, within step (iii), said source of silicon is combined with said primary mixture prior to adding said at least one organic template.

Embodiment 14

The method of embodiment 12 or embodiment 13, wherein said primary mixture and said source of silicon are combined to form a secondary mixture for a time and under conditions sufficient to allow homogenization of the secondary mixture, physico-chemical interaction between said source of silicon and said primary mixture, or both, after which said at least one organic template is combined therewith.

Embodiment 15

The method of any of embodiments 1-3 and 5-14, wherein one or more of the following are satisfied: the source of aluminum comprises alumina; the source of phosphorus comprises phosphoric acid; the source of silicon comprises an organosilicate comprising a tetraalkylorthosilicate; and the at least one organic template comprises N,N-dimethylcyclohexylamine.

Embodiment 16

The method of any of the previous embodiments, wherein step (b) was accomplished using seeds having a framework type of CHA, AEI, AFX, LEV, an intergrowth thereof, or a combination thereof.

Embodiment 17

The method of any of embodiments 3-4, 7-9, and 11-16, wherein said reaction mixture is retained within said crystallization temperature range for a period of less than 5 hours.

Embodiment 18

The method of any of the previous embodiments, wherein said reaction mixture is substantially free of fluoride ions.

Embodiment 19

The method of any of embodiments 2-18, wherein the hydrocarbon feed is an oxygenate-containing feed comprising methanol, dimethylether, or a combination thereof, and wherein the one or more olefins comprises ethylene, propylene, or a combination thereof.

Embodiment 20

A method of forming an olefin-based polymer product comprising: (1) preparing a product comprising predominantly one or more olefins according to any of embodiments 2-19; and (2) polymerizing at least one of the one or more olefins, optionally with one or more other comonomers and optionally in the presence of a polymerization catalyst, under conditions sufficient to form an olefin-based (co)polymer.

Embodiment 21

The method of embodiment 20, wherein the hydrocarbon feed is an oxygenate-containing feed comprising methanol, dimethylether, or a combination thereof, wherein the one or more olefins comprises ethylene, propylene, or a combination thereof, and wherein the olefin-based (co)polymer is an ethylene-containing (co)polymer, a propylene-containing (co)polymer, or a copolymer, mixture, or blend thereof.

The invention will now be more particularly described with reference to the following Examples and the accompanying drawings.

EXAMPLES

The analysis techniques described below were among those used in characterizing various samples from the Examples.

ICP-OES

Elemental analysis has been done using ICP-OES (Inductively Coupled Plasma—Optical Emission Spectrometry). Samples were dissolved in a mixture of acids and diluted in deionized water. The instrument (Simultaneous VISTA-MPX from Varian) was calibrated using commercial available standards (typically at least 3 standards and a blank). The power used was about 1.2 kW, plasma flow about 13.5 L/min, and nebulizer pressure about 200 kPa for all lines. Results are expressed in wt % or ppm by weight (wppm), and the values are recalculated to $Si/Al_2$ molar ratios.

XRD

Either of two X-ray diffractometers was used: a STOE Stadi-P Combi Transmission XRD and a Scintag X2 Reflection XRD with optional sample rotation. $Cu-K_\alpha$ radiation was used. Typically, a step size of 0.2° 2Θ and a measurement time of about 1 hour were used.

SEM

A JEOL JSM-6340F Field-Emission-Gun scanning electron microscope (SEM) was used, operating at about 2 kV and about 12 µA. Prior to measurement, samples were dispersed in ethanol, subjected to ultrasonic treatment for about 5 to about 30 minutes, deposited on SEM sample holders, and dried at room temperature and pressure (about 20-25° C. and about 101 kPa). If an average particle size was determined based on the SEM micrographs, typically the measurement was performed on at least 30 crystals. In case of the near cubic crystals, the average was based on the sizes of one of the edges of each crystal.

PSA

Particle size analysis was performed using a Mastersizer APA2000 from Malvern Instruments Limited, equipped with a 4 mW laser beam, based on laser scattering by randomly moving particles in a liquid medium. The samples to be measured were dispersed in water under continuous ultrasonic treatment to ensure proper dispersion. The pump speed applied was 2000 RPM, and the stirrer speed was 800 RPM. The parameters used in the operation procedure were: Refractive Index=1.544, Absorption=0.1. The results were calculated using the "general purpose-enhanced sensitivity" model. The results were expressed as $d_{50}$, meaning that 50 vol % of the particles were smaller than the value. The average of at least 2 measurements, with a delay of at least about 10 seconds, was reported.

Comparative Example A

A synthesis mixture having a molar composition of about $0.11\ SiO_2:P_2O_5:Al_2O_3:2\ DMCHA:40H_2O$, as well as 100 wt ppm seeds, was prepared according to the following procedure. A solution of phosphoric acid was prepared by combining phosphoric acid [Acros 85%] and water. To this solution was added the appropriate amount of Condea Pural SB [Sasol, 75.6 wt % $Al_2O_3$] and the slurry was stirred for about 1 hour at about 10° C. To this mixture was added the appropriate amount of TEOS [tetraethyorthosilicate from Aldrich]. Then the appropriate amount of dimethylcyclohexylamine [DMCHA from Purum Fluka] was added. This mixture was stirred for about 10 minutes before the seeds (SAPO-34 seeds) were added. The final mixture was transferred to an autoclave which was stirred and heated to about 170° C. with a heat-up rate of about 5° C./hr. Immediately after reaching this temperature, the autoclave was cooled to approximately room temperature (about 20-25° C.), and the solids were washed with demineralized water and dried at about 120° C. The yield was determined by weighing the dried solids and dividing this weight by the weight of the initial synthesis mixture. The so-calculated yield was about 6.6 wt %. The phase purity of the sample was determined by X-ray diffraction and was characterized substantially by the d-spacings shown in Table 1 above. SEMs were recorded and the crystal size was determined to be, on average, approximately 1.3 µm. The $d_{50}$, as determined by PSA, was approximately 1.2 µm.

Comparative Examples B-D

A series of samples was made according to the same procedure, but only changing the $Si/Al_2$ ratio of the synthesis mixture. All products resulted in materials characterized substantially by the d-spacings shown in Table 1 above, with an average crystal size around 1 µm or larger. The $d_{50}$, as determined by PSA, and the yield results are summarized in Table 2. SEM micrographs of Comparative Examples A-D are shown in FIGS. 1-4.

TABLE 2

Yield and $d_{50}$ [μm] of products made according to Comparative Examples A-D with a heat-up rate of about 5° C./hr and various $Si/Al_2$ ratios in the mixture.

| Compar. Ex. | $Si/Al_2$ | Yield % | $d_{50}$ |
|---|---|---|---|
| A | 0.11 | 6.6 | 1.2 |
| B | 0.12 | 7.3 | 1.3 |
| C | 0.13 | 7.5 | 1.0 |
| D | 0.14 | 7.5 | 0.9 |

Example 1

A synthesis mixture having a molar composition of about 0.11 $SiO_2:P_2O_5:Al_2O_3$:2 DMCHA:40$H_2O$, as well as 100 wt ppm seeds, was prepared according to the following procedure. A solution of phosphoric acid was prepared by combining phosphoric acid [Acros 85%] and water. To this solution was added the appropriate amount of Condea Pural SB [Sasol, 75.6 wt % $Al_2O_3$] and the slurry was stirred for about 1 hour at about 1° C. To this mixture was added the appropriate amount of TEOS [tetraethyorthosilicate from Aldrich]. Then the appropriate amount of dimethylcyclohexylamine [DMCHA from Purum Fluka] was added. This mixture was stirred for about 10 minutes before the seeds (SAPO-34 seeds) were added. The final mixture was transferred to an autoclave which was stirred and heated to about 170° C. with a heat-up rate of about 40° C./hr, while stirring, and was kept under these conditions for about 24 hours. After this time, the autoclave was cooled to approximately room temperature, and the solids were washed with demineralized water and dried at about 120° C. The yield was determined by weighing the dried solids and dividing this weight by the weight of the initial synthesis mixture. The so-calculated yield was about 10.5 wt %. The phase purity of the sample was determined by X-ray diffraction and was characterized substantially by the d-spacings shown in Table 1 above. SEMs were recorded and the crystal size was determined to be, on average, approximately 0.4 μm. The $d_{50}$, as determined by PSA, was approximately 0.7 μm.

Examples 2-4

A series of samples was made according to the same procedure, but only changing the $Si/Al_2$ ratio of the synthesis mixture. All products resulted in materials characterized substantially by the d-spacings shown in Table 1 above, with an average crystal size of about 0.4 μm. The $d_{50}$, as determined by PSA, and the yield results are summarized in Table 3. SEM photographs of Examples 1-4 are shown in FIGS. 5-8.

TABLE 3

Yield and $d_{50}$ [μm] of products made according to Examples 1-4 with a heat-up rate of about 40° C./hr and various $Si/Al_2$ ratios in the mixture.

| Example | $Si/Al_2$ | Yield % | $d_{50}$ |
|---|---|---|---|
| 1 | 0.11 | 10.5 | 0.7 |
| 2 | 0.12 | 11.1 | 0.6 |
| 3 | 0.13 | 10.2 | 0.6 |
| 4 | 0.14 | 10.6 | 0.6 |

As can be seen from Tables 2-3 and FIGS. 1-8, applying the faster heat-up rate for crystallization causes a relatively smaller average crystal size, even with a longer duration of heating at the crystallization temperature (in this case, about 170° C.).

Example 5

Figure 9:
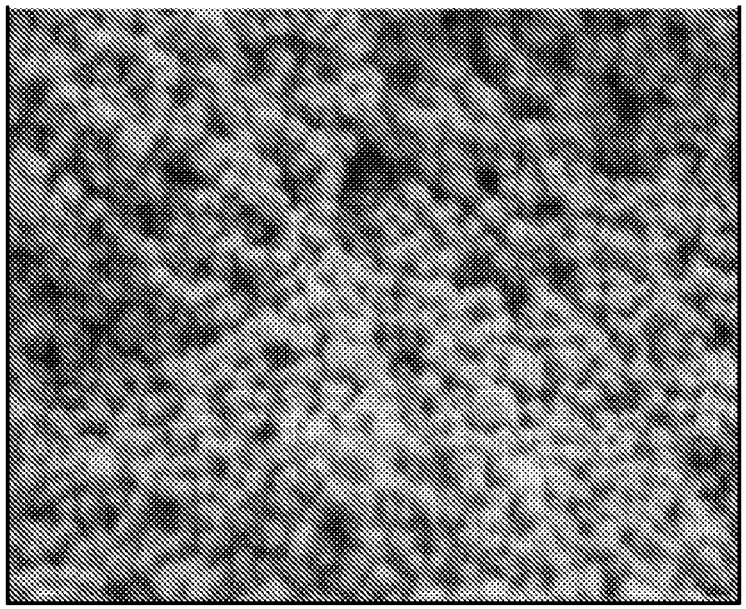
FIG. 9 shows an SEM micrograph of a molecular sieve made according to Example 5 and recovered after zero hours at the crystallization temperature (sample 5A).
Figure 10:
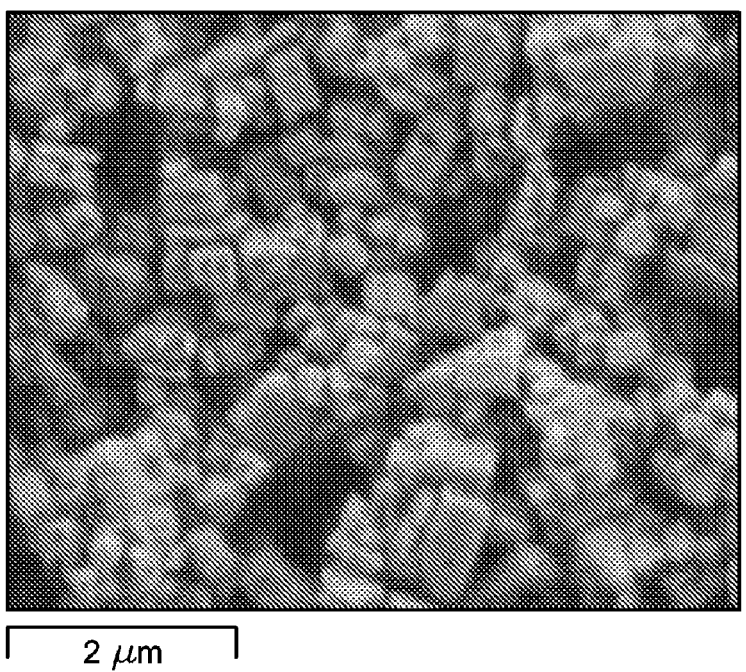
FIG. 10 shows an SEM micrograph of a molecular sieve made according to Example 5 and recovered after 10 hours at the crystallization temperature (sample 5B).

A synthesis mixture having a molar composition of about 0.05 $SiO_2:P_2O_5:Al_2O_3$: 2 DMCHA:40$H_2O$, as well as 100 wt ppm seeds, was prepared according to the following procedure. A solution of phosphoric acid was prepared by combining phosphoric acid [Acros 85%] and water. To this solution was added the appropriate amount of Condea Pural SB [Sasol, 75.6 wt % $Al_2O_3$] and the slurry was stirred for about 1 hour at about 1° C. To this mixture was added the appropriate amount of TEOS [tetraethyorthosilicate from Aldrich]. Then the appropriate amount of dimethylcyclohexylamine [DMCHA from Purum Fluka] was added. This mixture was stirred for about 10 minutes before the seeds (SAPO-34 seeds) were added. The final mixture was transferred to an autoclave which was stirred and heated to about 170° C. with a heat-up rate of about 40° C./hr, while stirring, and was kept under these conditions for about 0 hours [sample 5A] or for about 10 hrs [sample 5B]. After this time, the autoclave was cooled to approximately room temperature, and the solids were washed with demineralized water and dried at about 120° C. The yield was determined by weighing the dried solids and dividing this weight by the weight of the initial synthesis mixture. The so-calculated yield was about 1.5 wt % after about 0 hours and about 8 wt % after about 10 hours. SEMs were recorded and the crystal size was determined to be, on average, approximately 0.5 μm after about 0 hours and approximately 2 μm after about 10 hours. The crystals appear to have grown larger during the extra time at about 170° C. The SEM pictures of Samples 5A and 5B are shown in FIGS. 9 and 10, respectively.

Comparative Examples E-H

A series of samples was prepared having a molar composition of $xSiO_2:P_2O_5:Al_2O_3$:2 DMCHA:40$H_2O$, as well as 100 wt ppm seeds, with x varying from about 0.02 to about 0.05, in approximately 0.01 increments. The mixtures were prepared according to the following procedure. A solution of phosphoric acid was prepared by combining phosphoric acid [Acros 85%] and water. To this solution was added the appropriate amount of Condea Pural SB [Sasol, 75.6 wt % $Al_2O_3$] and the slurry was stirred for about 10 minutes at about 10° C. To this mixture was added the appropriate amount of TEOS [tetraethyorthosilicate from Aldrich]. Then the appropriate amount of dimethylcyclohexylamine [DMCHA from Purum Fluka] was added. This mixture was stirred for about 10 minutes before the seeds (SAPO-34 seeds) were added. This mixture was transferred to an autoclave which heated to about 170° C. with a heat-up rate of about 5° C./hr, while stirring, and was kept under these conditions for about 120 hours. After this time, the autoclave was cooled to approximately room temperature, and the solids were washed with demineralized water and dried at about 120° C. The yield was determined by weighing the dried solids and dividing this weight by the weight of the initial synthesis mixture. In all cases, the phase purity of each sample was determined by X-ray diffraction and was characterized substantially by the d-spacings shown in Table 1 above. The yield results are summarized in Table 4.

TABLE 4

Yield of products made according to Comparative Examples E-H made with a heat-up rate of about 5° C./hr and various Si/Al$_2$ ratios in the mixture.

| Compar. Ex. | Si/Al$_2$ | Yield % |
|---|---|---|
| E | 0.02 | 15.0 |
| F | 0.03 | 15.1 |
| G | 0.04 | 15.5 |
| H | 0.05 | 15.6 |

Examples 6-9

A set of mixtures with the same molar composition as in Comparative Examples E-H was prepared, but was crystallized under slightly different conditions. Each mixture was transferred to an autoclave which was heated to about 170° C. with a heat-up rate of about 40° C./hr, while stirring, and was kept under these conditions for about 120 hours. After this time, the autoclave was cooled to approximately room temperature, and the solids were washed with demineralized water and dried at about 120° C. The yield was determined by weighing the dried solids and dividing this weight by the weight of the initial synthesis mixture. In all cases, the phase purity of each sample was determined by X-ray diffraction and was characterized substantially by the d-spacings shown in Table 1 above. The yield results are summarized in Table 5.

TABLE 5

Yield of products made according to Examples 6-9 with a heat-up rate of about 40° C./hr and various Si/Al$_2$ ratios in the mixture.

| Example | Si/Al$_2$ | Yield % |
|---|---|---|
| 6 | 0.02 | 8.6 |
| 7 | 0.03 | 8.2 |
| 8 | 0.04 | 8.6 |
| 9 | 0.05 | 8.7 |

Catalytic Evaluation of Comparative Examples E-H Versus Examples 6-9

Figure 11:
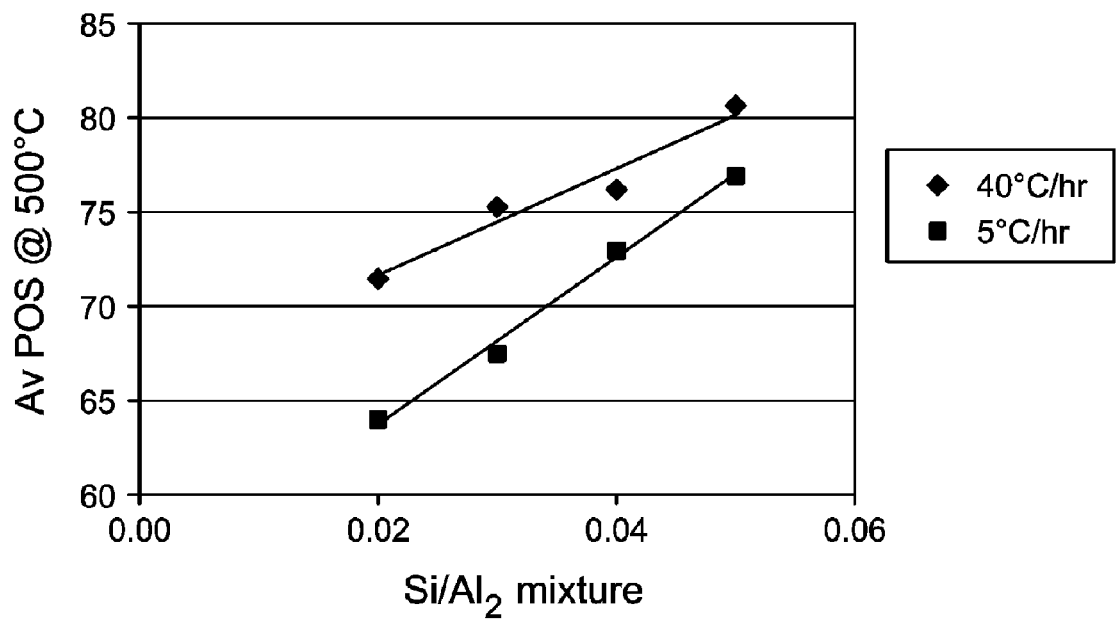
FIG. 11 shows a graph of the MTO performance of the molecular sieves from Table 6.

Each sample was tested for hydrocarbon conversion performance in an automated methanol-to-olefins (MTO) performance testing instrument. Test conditions involved addition of about 20 mg of sieve crystals calcined from Comparative Examples E-H and Examples 6-9 into a ~4 mm ID tubular reactor along with about 200 mg of silicon carbide (SiC, inert diluent). A vaporized stream of methanol was introduced at an average bed temperature of about 500° C., a WHSV of about 100 grams MeOH per gram of sieve per hour, and a total pressure of about 25 psig (about 273 kPag). Samples were periodically collected and analyzed by gas chromatography for about 20 minutes and were mathematically integrated to arrive at a conversion weighted average set of selectivities for each aged or un-aged sieve. The average combined ethylene and propylene selectivity, expressed as prime olefin selectivity (POS), are compared in Table 6 below and are represented in FIG. 11.

It is noteworthy that, under these conditions, a higher heat-up rate (about 40° C./hr vs about 5° C./hr) not only results in relatively smaller crystal size (which is preferred, in this case), but also attains a higher POS when used as a catalyst in MTO reactions (which is also preferred in this case). In other words, a higher POS can be obtained with samples that are prepared from the same chemical composition but that are heated at a faster rate to the crystallization temperature.

TABLE 6

Average prime olefin selectivity [av POS] at about 500° C. for each sample.

| Example | Si/Al$_2$ | Heat-up rate | av POS |
|---|---|---|---|
| E | 0.02 | 5° C./hr | 64.1 |
| F | 0.03 | 5° C./hr | 67.6 |
| G | 0.04 | 5° C./hr | 72.9 |
| H | 0.05 | 5° C./hr | 77.1 |
| 6 | 0.02 | 40° C./hr | 71.6 |
| 7 | 0.03 | 40° C./hr | 75.4 |
| 8 | 0.04 | 40° C./hr | 76.3 |
| 9 | 0.05 | 40° C./hr | 80.6 |

Comparative Example I

A synthesis mixture having a molar composition of about 0.02 SiO$_2$:P$_2$O$_5$:Al$_2$O$_3$:2DMCHA:40H$_2$O, as well as 100 wt ppm seeds, was prepared according to the following procedure. A solution of phosphoric acid was prepared by combining phosphoric acid [Acros 85%] and water. To this solution was added the appropriate amount of Condea Pural SB [Sasol, 75.6 wt % Al$_2$O$_3$] and the slurry was stirred for about 1 hour at about 10° C. To this mixture was added the appropriate amount of TEOS [tetraethyorthosilicate from Aldrich]. Then the appropriate amount of dimethylcyclohexylamine [DMCHA from Purum Fluka] was added. This mixture was stirred for about 10 minutes before the seeds (SAPO-34 seeds) were added.

The final mixture was transferred to an autoclave which was stirred and heated to about 170° C. with a heat-up rate of about 40° C./hr. After about 24 hours at this temperature, the autoclave was cooled to approximately room temperature (about 20-25° C.), and the solids were washed with demineralized water and dried at about 120° C. The yield was determined by weighing the dried solids and dividing this weight by the weight of the initial synthesis mixture. The so-calculated yield was about 8.5 wt %. The phase purity of the sample was determined by X-ray diffraction and was characterized substantially by the d-spacings shown in Table 1 above. The $d_{50}$, as determined by PSA, was approximately 1.2 μm.

Comparative Examples J-L

Figure 12:
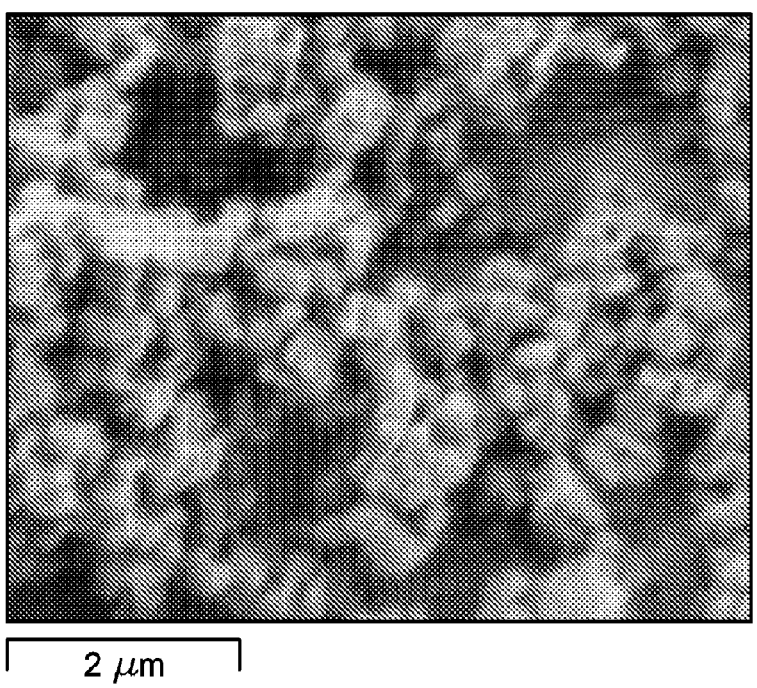
FIG. 12 shows an SEM micrograph of a molecular sieve made according to Comparative Example L.

A series of samples was made according to the same procedure, but only changing the Si/Al$_2$ ratio of the synthesis mixture. All products resulted in materials characterized substantially by the d-spacings shown in Table 1 above, with an average crystal size around 1 μm or larger. The $d_{50}$, as determined by PSA, and the yield results are summarized in Table 7. An SEM micrograph of Comparative Example M is shown in FIG. 12.

TABLE 7

Yield and $d_{50}$ [μm] of products made according to Comparative Examples I-L with various Si/Al$_2$ ratios in the mixture.

| Example | Si/Al$_2$ | Heating rate | Yield % | $d_{50}$ |
|---|---|---|---|---|
| I | 0.02 | 40° C./hr | 8.5 | 1.2 |
| J | 0.03 | 40° C./hr | 7.9 | 1.2 |
| K | 0.04 | 40° C./hr | 7.9 | 1.0 |
| L | 0.05 | 40° C./hr | 7.9 | 1.1 |

Examples 10-13

A set of mixtures with the same molar composition as in Comparative Examples I-L were prepared but was crystallized under slightly different conditions. Each mixture was transferred to an autoclave which was heated to about 170° C. with a heat-up rate of about 5° C./hr, while stirring. When the autoclaves reached about 170° C., the autoclave was cooled to approximately room temperature, and the solids were washed with demineralized water and dried at about 120° C. The yield was determined by weighing the dried solids and dividing this weight by the weight of the initial synthesis mixture. In all cases, the phase purity of each sample was determined by X-ray diffraction and was characterized substantially by the d-spacings shown in Table 1 above. The results of the experiments are summarized in Table 8.

TABLE 8

Yield and $d_{50}$ [μm] of products made according to Examples 10-13 with various $Si/Al_2$ ratios in the mixture.

| Example | $Si/Al_2$ | Heating rate | Yield % | $d_{50}$ |
|---|---|---|---|---|
| 10 | 0.02 | 5° C./hr | 1.5 | 3.8 |
| 11 | 0.03 | 5° C./hr | 2.2 | 3.9 |
| 12 | 0.04 | 5° C./hr | 3.0 | 0.9 |
| 13 | 0.05 | 5° C./hr | 3.3 | 0.7 |

Figure 13:
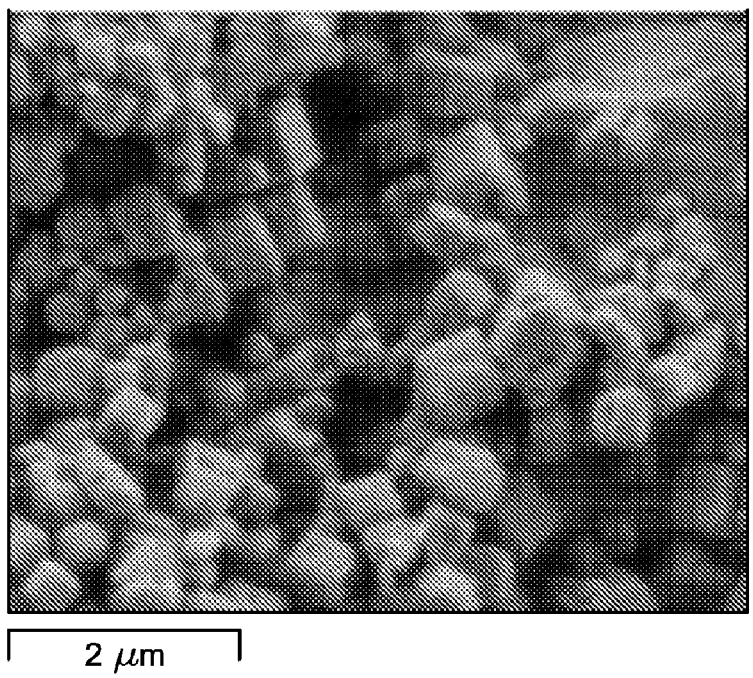
FIG. 13 shows an SEM micrograph of a molecular sieve made according to Example 12.

The yields for Examples 10-13 were smaller than in Comparative Examples I-L. The $d_{50}$ of the materials, as determined by PSA, indicated somewhat larger crystals. However, SEM micrographs of some of these Examples showed that the measured $d_{50}$ values were not representative for the average crystal size. As an example, a representative SEM micrograph of Example 12 is shown in FIG. 13.

Example 14

Catalytic Evaluation

Figure 14:
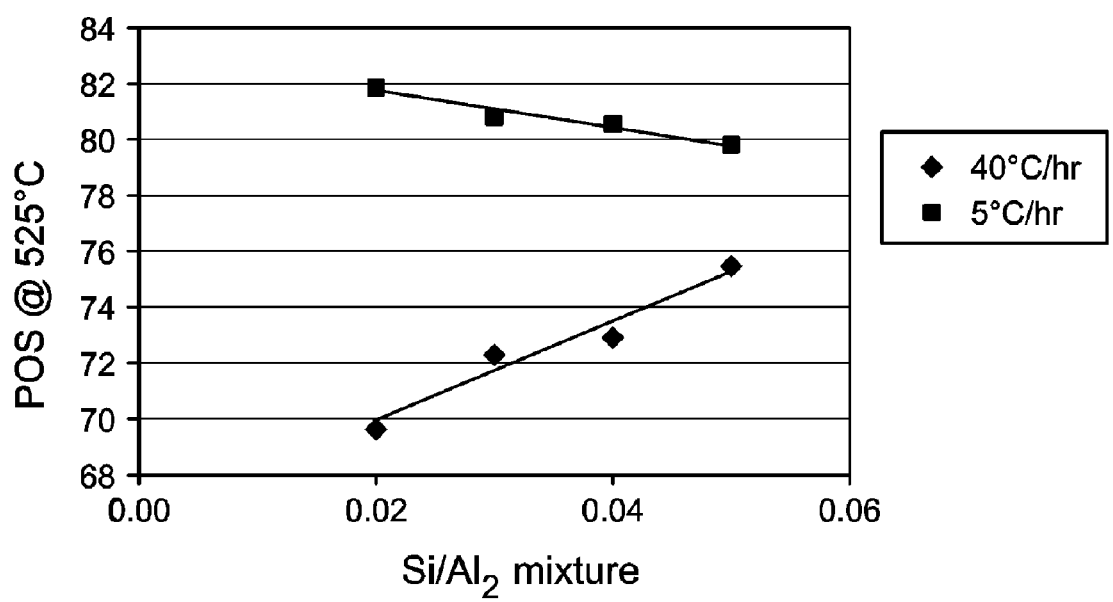
FIG. 14 shows a graph of the MTO performance of the molecular sieves from Table 9.

Each sample from Examples 10-13 and Comparative Examples I-L was tested for hydrocarbon conversion performance in an automated methanol-to-olefins (MTO) performance testing instrument. Test conditions involved addition of about 20 mg of sieve crystals calcined from Comparative Examples I-L and Examples 10-13 into a ~4 mm ID tubular reactor along with about 200 mg of silicon carbide (SiC, inert diluent). A vaporized stream of methanol was introduced at an average bed temperature of about 525° C., a WHSV of about 100 grams MeOH per gram of sieve per hour, and a total pressure of about 25 psig (about 273 kPag). Samples were periodically collected and analyzed by gas chromatography for about 20 minutes and were mathematically integrated to arrive at a conversion weighted average set of selectivities for each aged or un-aged sieve. The average combined ethylene and propylene selectivity, expressed as prime olefin selectivity (POS), are compared in Table 9 below and are represented in FIG. 14.

TABLE 9

Average prime olefin selectivity [av POS] at about 525° C. for each sample.

| Example | $Si/Al_2$ mixture | Heating Rate, ° C./hr | Average POS |
|---|---|---|---|
| I | 0.02 | 40 | 69.7 |
| J | 0.03 | 40 | 72.3 |
| K | 0.04 | 40 | 72.9 |
| L | 0.05 | 40 | 75.5 |
| 10 | 0.02 | 5 | 81.9 |
| 11 | 0.03 | 5 | 80.9 |
| 12 | 0.04 | 5 | 80.7 |
| 13 | 0.05 | 5 | 79.8 |

As can be seen from the results in Table 9, using reaction mixtures with similar chemical composition, the products obtained with the slower heat-up rate of about 5° C./hr, combined with a relatively short crystallization time, showed a higher POS in the oxygenates-to-olefins reaction than the products obtained with a faster heat-up rate or with a relatively longer crystallization time.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method of preparing a silicoaluminophosphate molecular sieve having a desired crystal size, the method comprising:
   (a) providing a synthesis mixture comprising a source of aluminum, a source of phosphorus, a source of silicon, and at least one organic template containing (i) a 4- to 8-membered cycloalkyl group, optionally substituted by 1-3 alkyl groups having from 1-3 carbon atoms, or (ii) a 4- to 8-membered heterocyclic group having from 1-3 heteroatoms, said heterocyclic group being optionally substituted by 1-3 alkyl groups having from 1-3 carbon atoms, and said heteroatoms in said heterocyclic groups being selected from the group consisting of O, N, and S, wherein the synthesis mixture exhibits a $Si/Al_2$ ratio less than 0.33;
   (b) inducing crystallization of a silicoaluminophosphate molecular sieve, which exhibits 90% or greater CHA framework type character, from said synthesis mixture by heating said synthesis mixture at a heating rate of more than 20° C./hr to a crystallization temperature; and
   (c) crystallizing said silicoaluminophosphate molecular sieve at the crystallization temperature for between 16 hours and 350 hours, such that a yield of silicoaluminophosphate molecular sieve greater than 8.0% is attained, wherein the crystallized silicoaluminophosphate molecular sieve exhibits a $Si/Al_2$ ratio less than 0.33 and has a crystal size distribution such that its average crystal size is not greater than 1.0 μm; and
   wherein step (a) comprises:
      (i) combining the source of phosphorus and the source of aluminum, optionally with a liquid mixture medium, to form a primary mixture;
      (ii) aging the primary mixture for an aging time and under aging conditions sufficient to allow homogenization of the primary mixture, physico-chemical interaction between the source of phosphorus and the source of aluminum, or both; and
      (iii) adding the source of silicon, the at least one organic template, and optionally additional liquid mixture medium, to the aged primary mixture to form the synthesis mixture, wherein said source of silicon is combined with said primary mixture prior to adding said at least one organic template.

2. The method of claim 1, wherein the at least one organic template comprises N,N-dimethylcyclohexylamine.

3. The method of claim 1, wherein the heating rate in step (b) is between 20° C./hr and 150° C./hr.

4. The method of claim 3, wherein said crystallization temperature is between 150° C. and 200° C.

5. The method of claim 1, wherein the crystallized silicoaluminophosphate molecular sieve from step (c) has a crystal size distribution such that the average crystal size is less than 0.9 μm.

6. The method of claim 1, wherein inducing step is done while stirring.

7. The method of claim 1, wherein said primary mixture and said source of silicon are combined to form a secondary mixture for a time and under conditions sufficient to allow homogenization of the secondary mixture, physico-chemical interaction between said source of silicon and said primary mixture, or both, after which said at least one organic template is combined therewith.

8. The method of claim 1, wherein the synthesis mixture and the crystallized silicoaluminophosphate molecular sieve both exhibit a $Si/Al_2$ ratio less than 0.33.

9. The method of claim 1, wherein one or more of the following are satisfied:
- the source of aluminum comprises alumina;
- the source of phosphorus comprises phosphoric acid;
- the source of silicon comprises an organosilicate comprising a tetraalkylorthosilicate; and
- the at least one organic template comprises N,N-dimethylcyclohexylamine.

10. The method of claim 1, wherein step (b) was accomplished using seeds having a framework type of CHA, AEI, AFX, LEV, an intergrowth thereof, or a combination thereof.

* * * * *